(12) United States Patent
Matsumoto

(10) Patent No.: US 6,177,106 B1
(45) Date of Patent: Jan. 23, 2001

(54) METHOD FOR FRACTIONATING RED BLOOD CELLS AND ANTIBACTERIAL MATERIALS FOR BACTERIAL PROLIFERATION INHIBITORS PRODUCED THEREBY

(76) Inventor: Tsukasa Matsumoto, 803 Estecion Oomori, 2-1-20, Oomorinaka, Oota-Ku, Tokyo 143 (JP)

( * ) Notice: Under 35 U.S.C. 154(b), the term of this patent shall be extended for 0 days.

(21) Appl. No.: 09/138,892

(22) Filed: Aug. 24, 1998

Related U.S. Application Data

(63) Continuation-in-part of application No. 08/803,458, filed on Feb. 20, 1997, now abandoned.

(30) Foreign Application Priority Data

Aug. 15, 1996 (JP) .................................................. 8-215552

(51) Int. Cl.[7] .......................... A61K 35/18; A61K 35/14; A01N 1/02

(52) U.S. Cl. ................................. 424/533; 424/529; 435/2

(58) Field of Search .................................. 435/2; 424/529, 424/533

Primary Examiner—Sandra E. Saucier
(74) Attorney, Agent, or Firm—Liniak, Berenato, Longarce & White, LLC

(57) ABSTRACT

A method for fractionating red blood cells of human blood into three fractions comprises following steps; (a) human blood sample is mixed with dextran aqueous solution and maintained stationarily for 60 to 75 min to fractionate this blood sample into three layers; (b) the upper, intermediate, and lower layer samples are individually separated and collected; and (c) the upper layer sample is treated with hypotonic solution for a short period and then added with hypertonic solution. Further the invention provides antibacterial or bacterial proliferation inhibitory material produced by the method. This method can easily fractionate three different blood fractions including red blood cells as a main component and having different functions. These three different fractions can be applied to several clinical tests such as antibacterial test and the like.

21 Claims, 34 Drawing Sheets

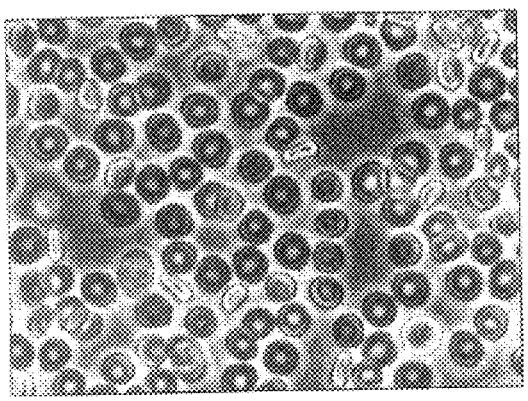
Fig. 1
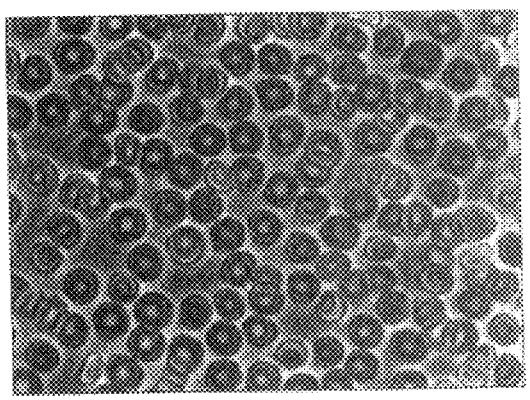
Fig. 5
Fig. 2
Fig. 3
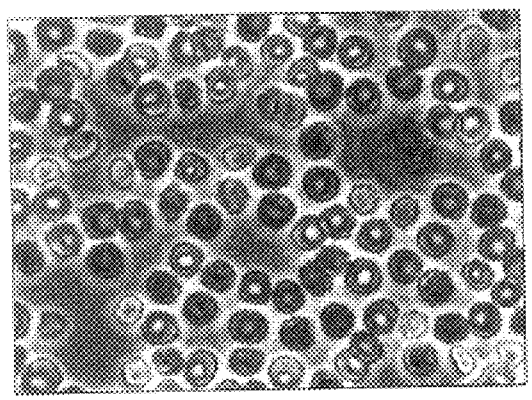
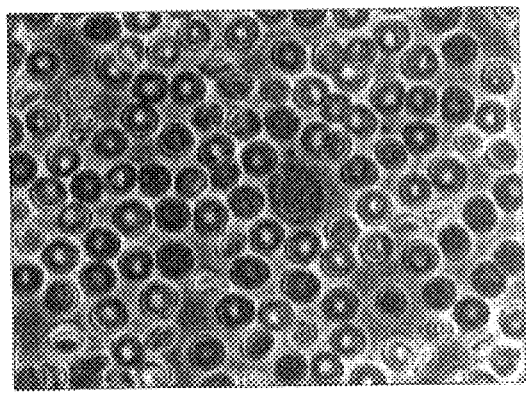
Fig. 4
Fig. 6
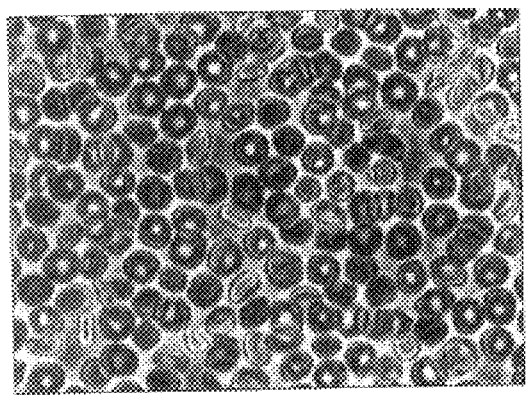
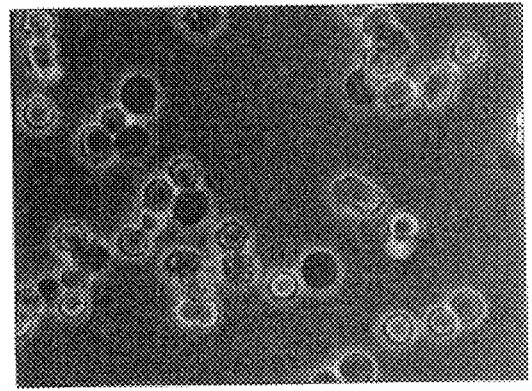

— LL
— IL
— UL

Fig. 9
A Group  RC-derived cells (Masked Erythrocyte) = Old Erythrocyte
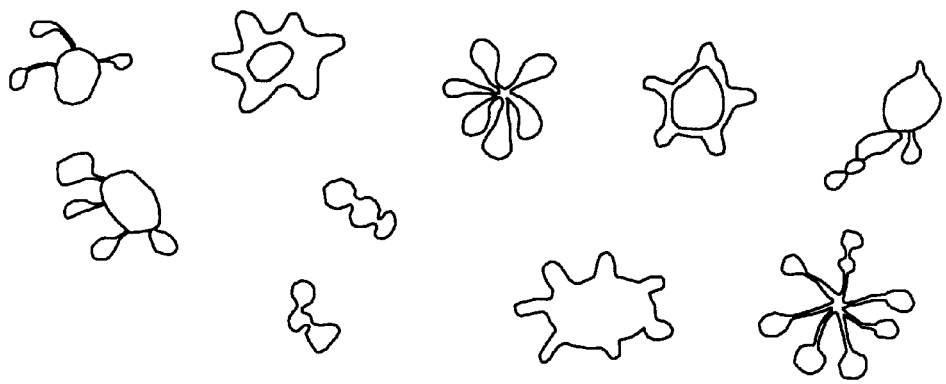
B Group  RC-derived cells (Masked Erythrocyte)
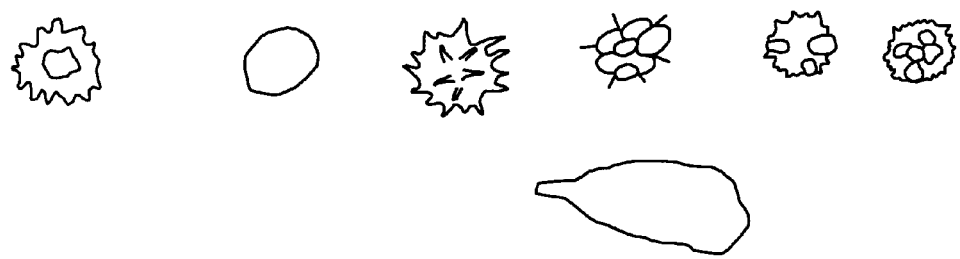
C Group  Non-Masked Erythrocyte (new erythrocyte)
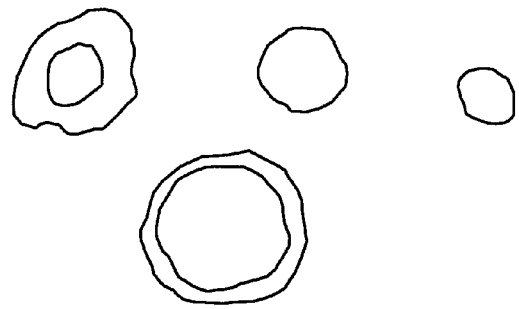

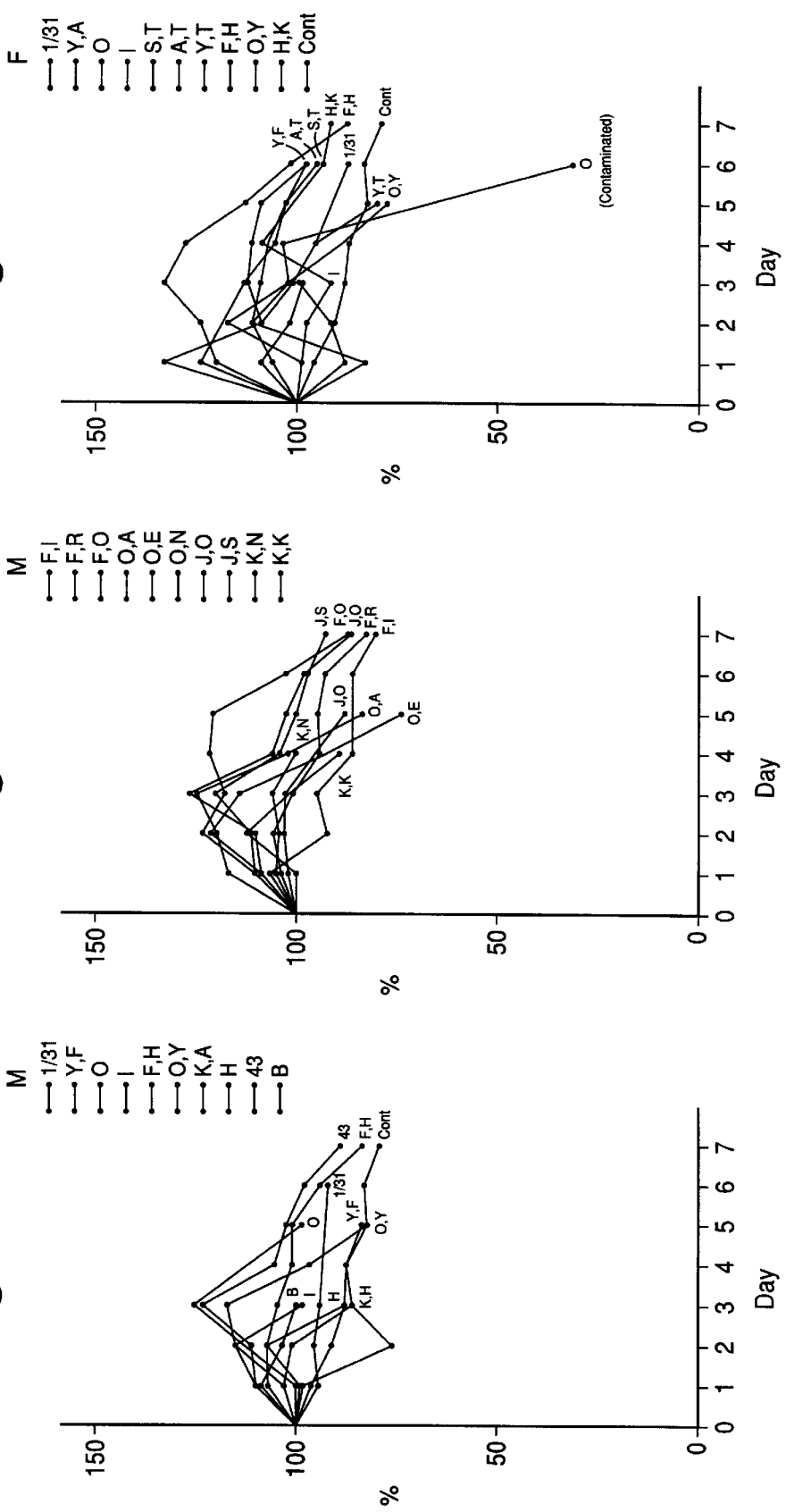

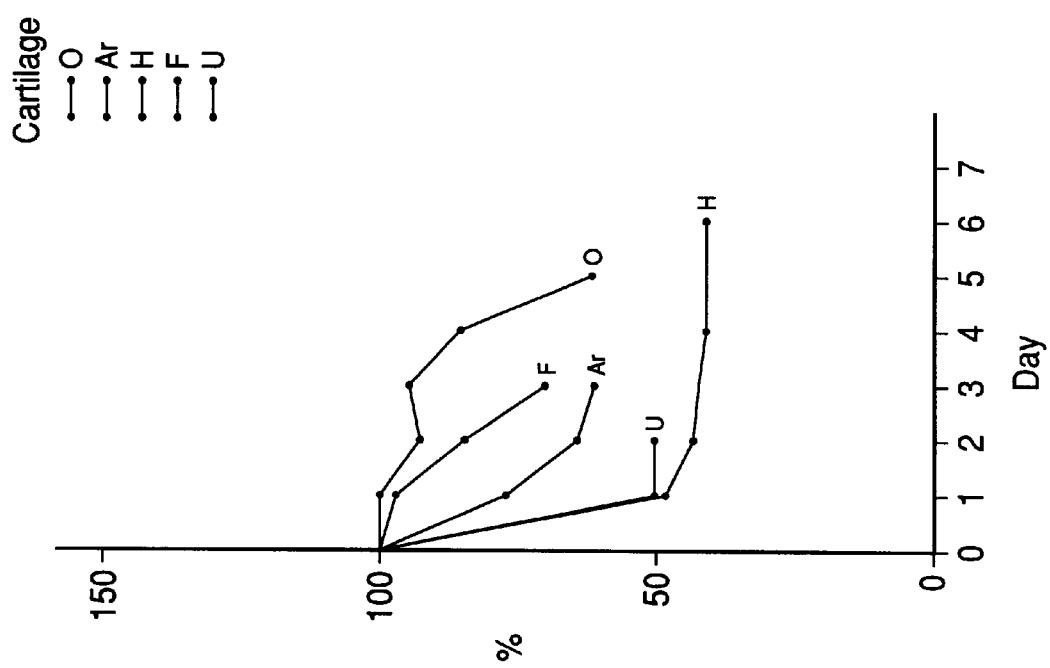

Fig. 71
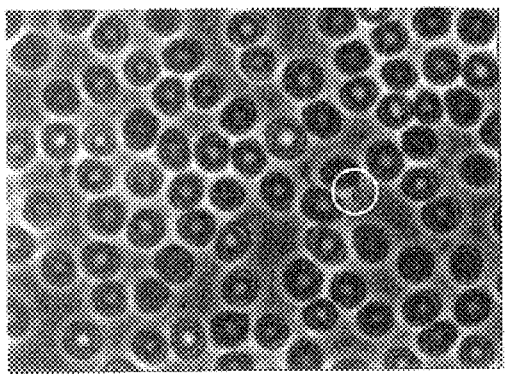
Fig. 72
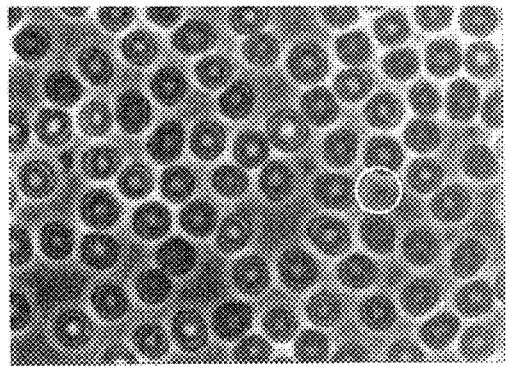
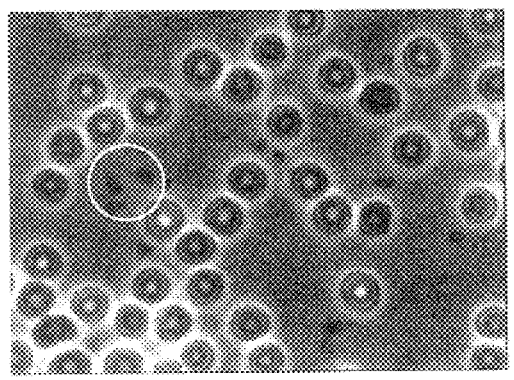
Fig. 73
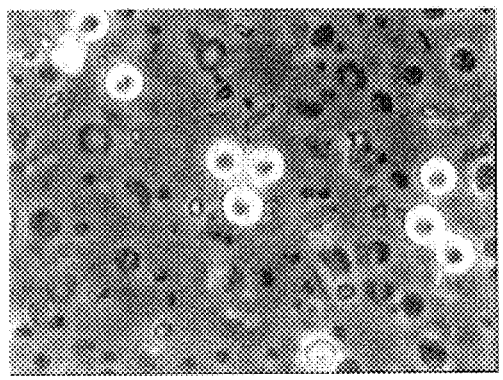
Fig. 74
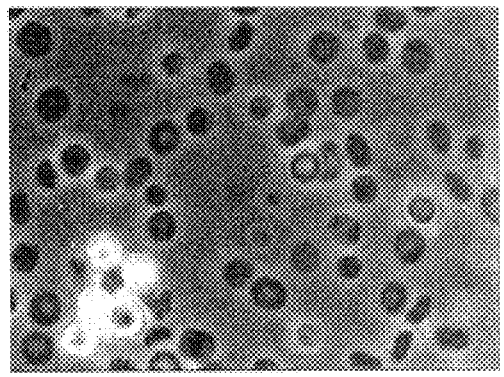
Fig. 75

Fig. 97
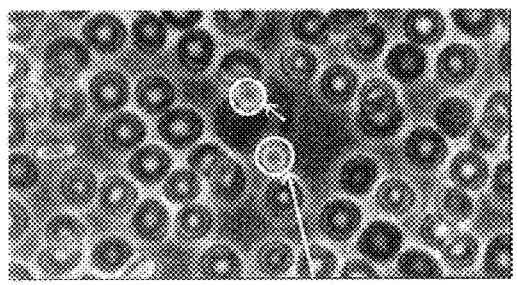
Fig. 98
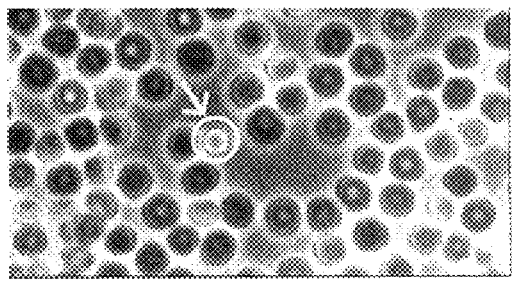
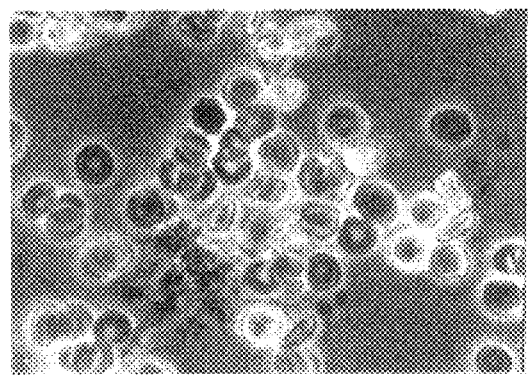
Fig. 99
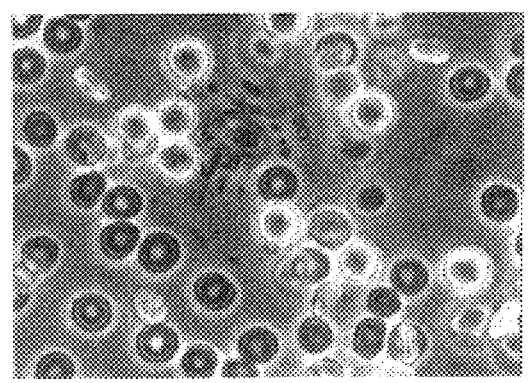
Fig. 100
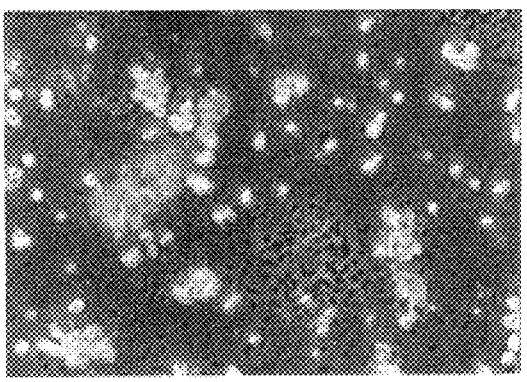
Fig. 101

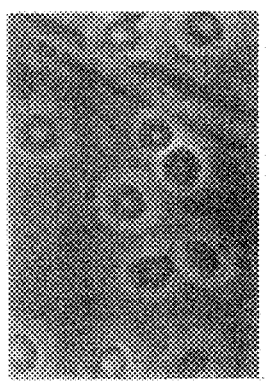
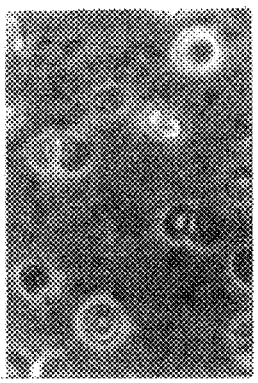
Fig. 120
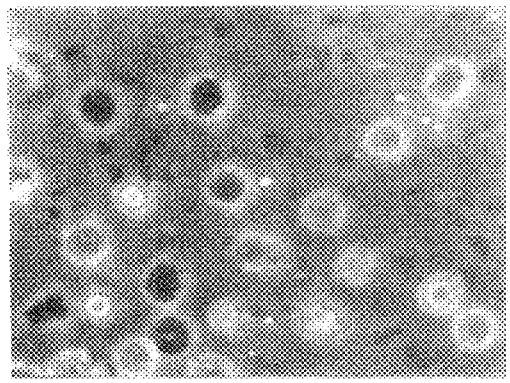
Fig. 123
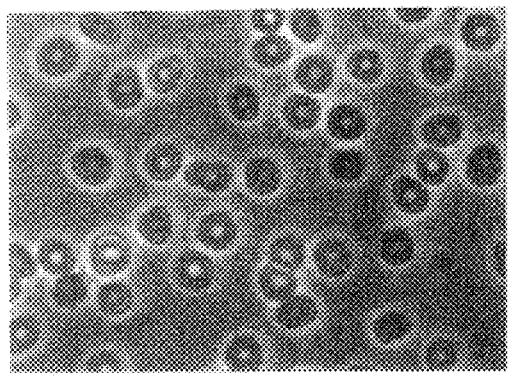
Fig. 121
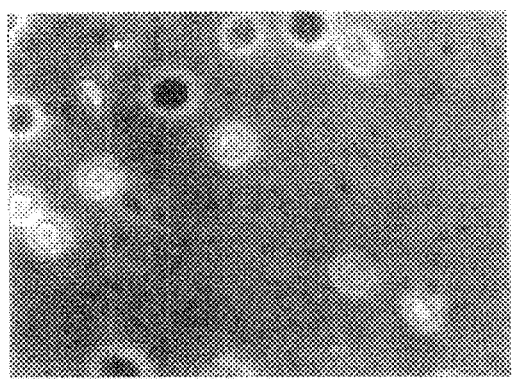
Fig. 124
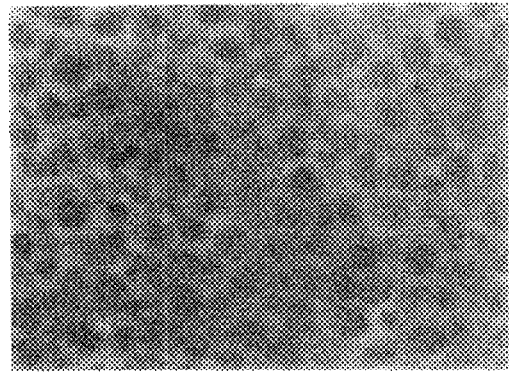
Fig. 122
Fig. 125

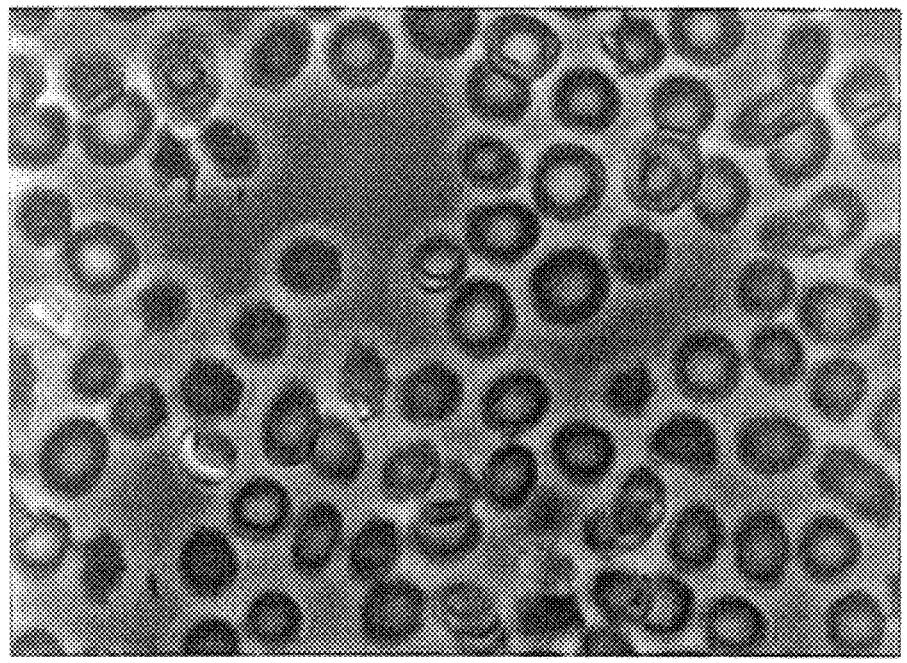
Fig. 132
Fig. 133
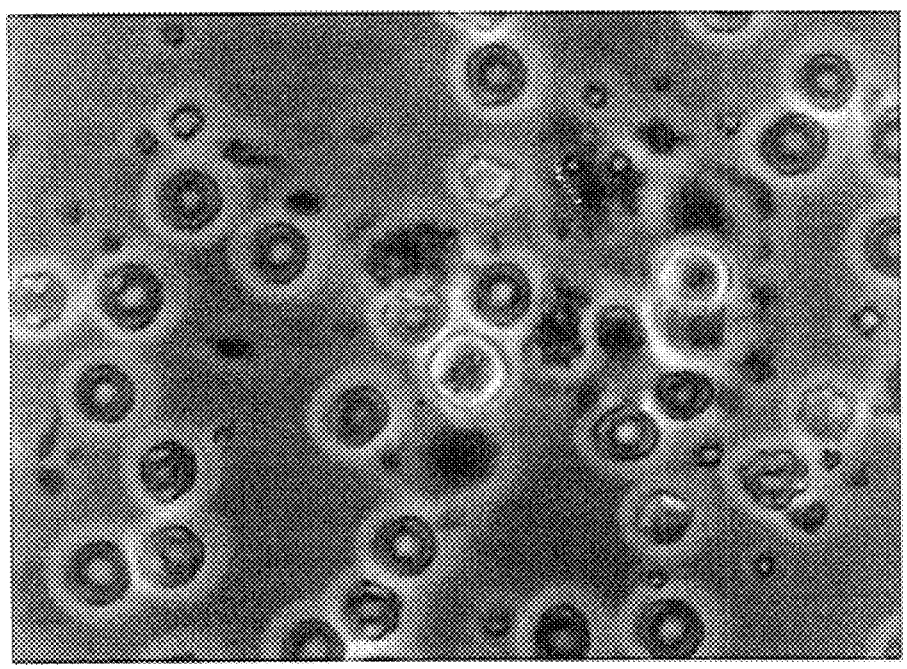

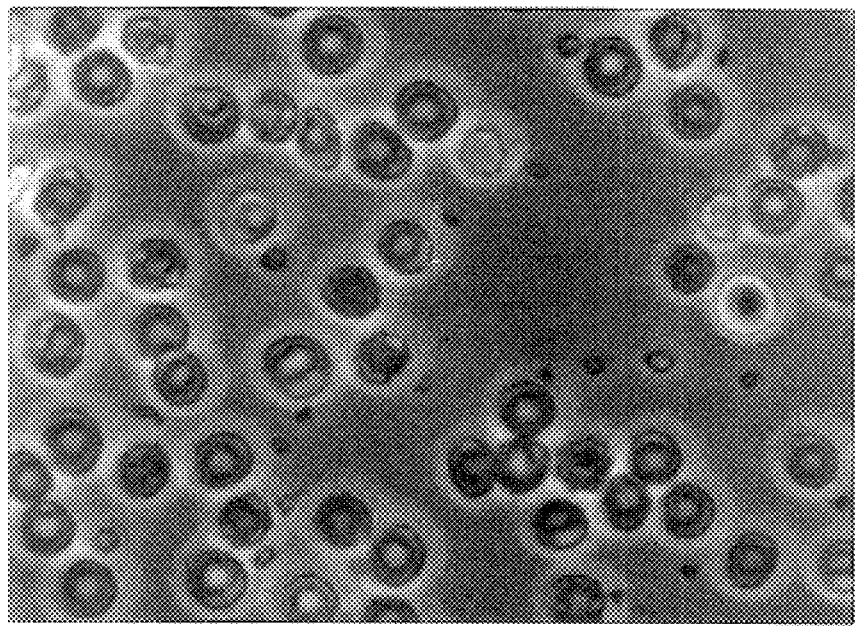
Fig. 134
Fig. 135
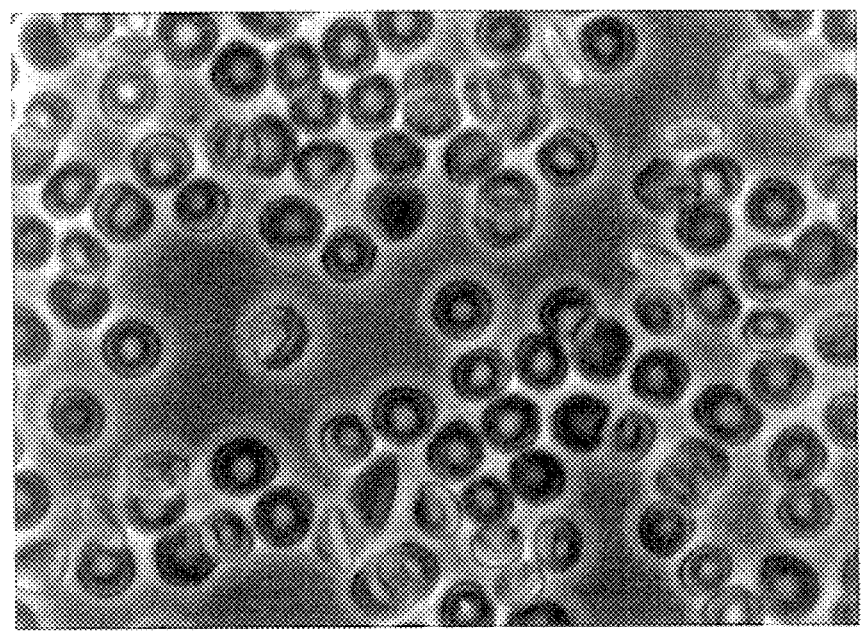

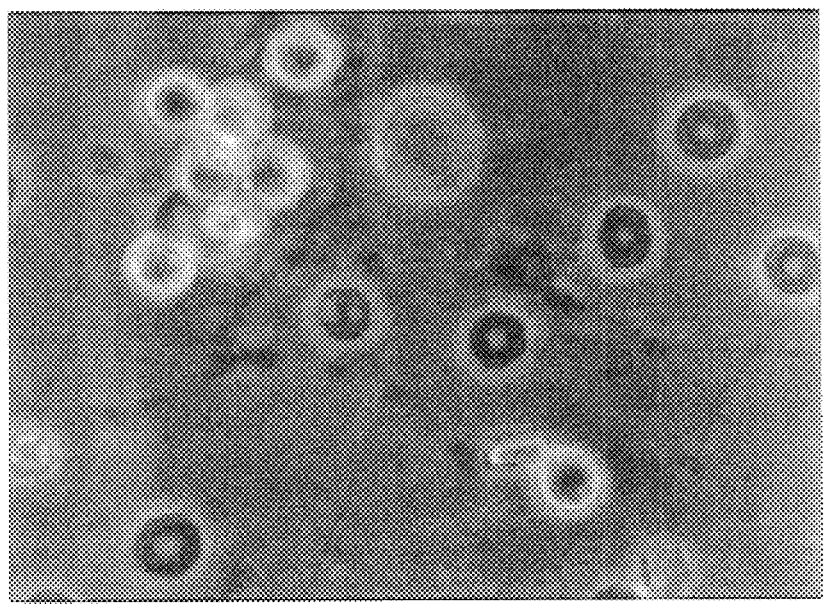
Fig. 136
Fig. 137
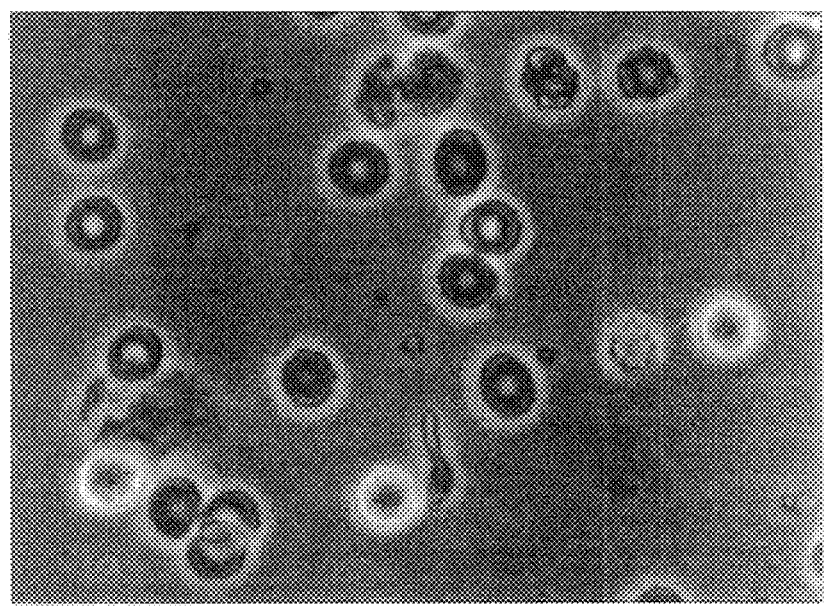

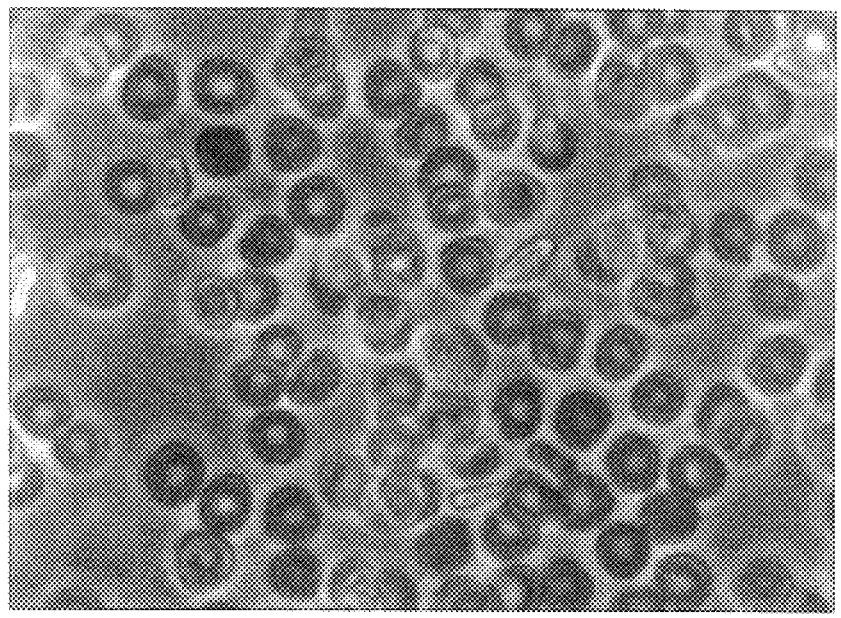
Fig. 138
Fig. 139
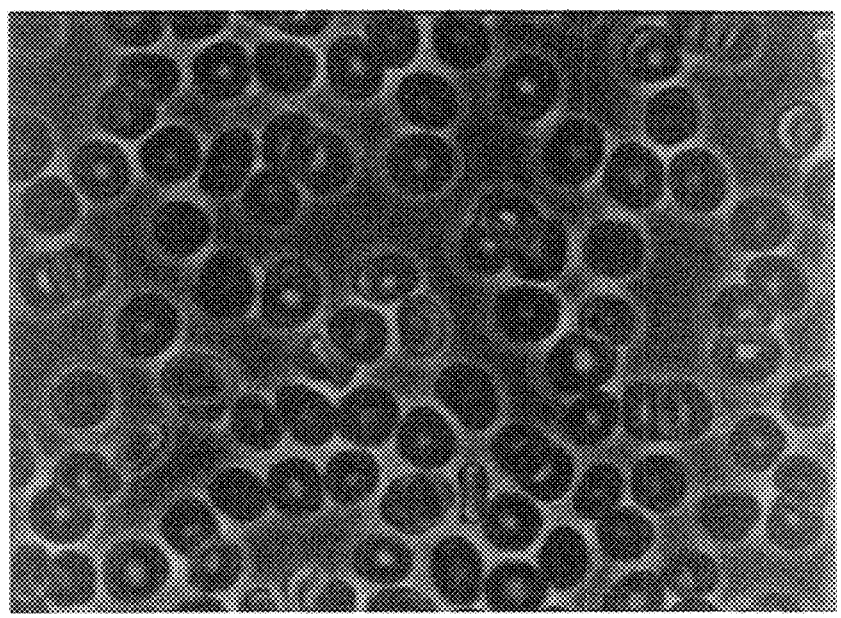

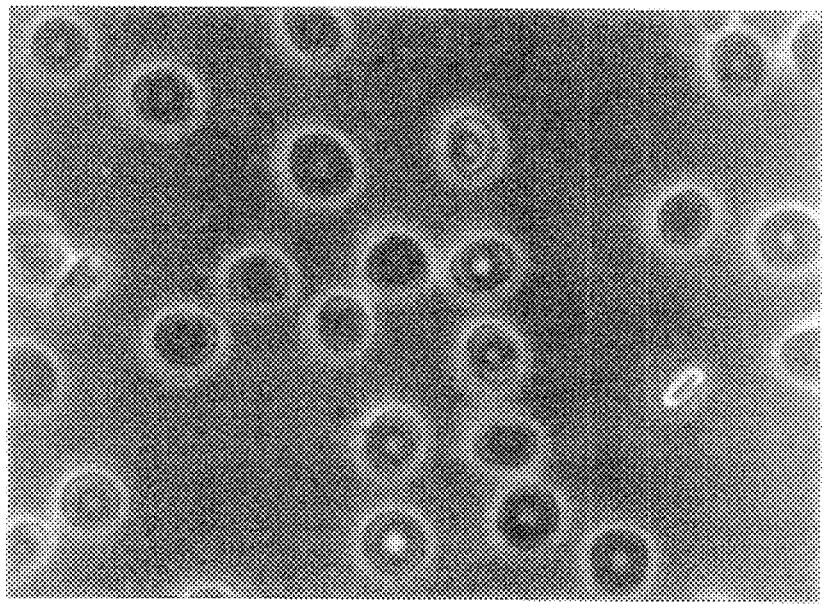
Fig. 140
Fig. 141
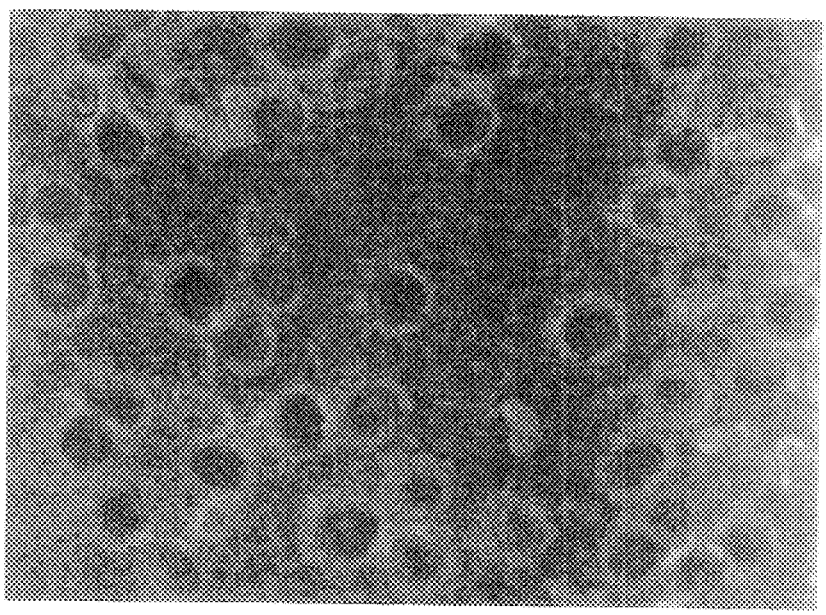

def

METHOD FOR FRACTIONATING RED BLOOD CELLS AND ANTIBACTERIAL MATERIALS FOR BACTERIAL PROLIFERATION INHIBITORS PRODUCED THEREBY

This application is a Continuation-in-Part of U.S. patent application Ser. No. 08/803,458 filed on Feb. 20, 1997 now abandoned and entitled "Method for Fractionating Red Blood Cells and Antibacterial Materials or Bacterial Proliferation Inhibitors Produced Thereby," the contents of which are incorporated herein by reference.

BACKGROUND OF THE INVENTION

The present invention relates to methods for fractionating red blood cells (RBC) of human blood into several fractions having different functions. Further the present invention relates to specific materials produced by such a method, which are possessed of antibacterial properties or inhibitory against bacterial proliferation.

Although it has been conventionally known that red blood cells of human blood act as carriers for carrying a large amount of oxygen and carbon dioxide at a high speed, the other functions of red blood cells have not yet been known completely. Notably, of the four signs of inflammation, rubor, calor, tumor, and dolor, the first three are caused by the congregation of red blood cells. The red blood cells that have gathered at the inflammatory site are estimated to have some action on the inflammation. However, in the past thirty years, there have been very few publications in this field.

A question pondered during the development of the present invention is whether the red blood cell truly is a single cell. The literature on the subject generally indicates that the red blood cell is a single cell. An experiment performed during development of the present invention, however, raised some doubt that the red blood cell is a single cell.

As part of the experiment, a drop of blood from a patient's cubital vein is extracted and then deposited into Costar's flask containing RPMI-1640. The contents of Costar's flask then is mixed. FIG. 1 illustrates an example of the resulting mixture. The mixture then is exposed to twenty minutes of sunlight which, in turn, produces the results illustrated in FIG. 2. The mixture then is incubated in a 5% $CO_2$, 37° C. incubator. FIG. 3 illustrates the condition of the mixture after 3.5 hours and FIG. 4 shows the condition of the mixture after 24 hours. For purposes of comparison, FIG. 5 shows an unprocessed mixture which is 24 hours old.

As FIG. 2 demonstrates, the cells change in shape and nature when exposed to 20 minutes of sunlight. Nevertheless, after twelve hours of incubation, many of the cells will recover to their original condition. Some cells, however, are unable to recover fully. After 24 hours, the so-called "ghost cells" appear.

Next, synovial fluid is extracted from patients with arthrosis deformans of the knee, rheumatoid arthritis, and the like, and a drop of blood of the same type as the patient's is added thereto. Also added to the synovial fluid is RPMI-1640 in a quantity of about 3 milliliters. FIG. 6 illustrates how the cells react. The way the red blood cells change is different depending on whether the red blood cells are those of patients suffering from arthrosis deformans of the knee or whether they are from patients afflicted with Rheumatoid arthritis.

The red blood cells therefore can be categorized into several types. Exposure to sunlight reveals five different types. The synovial fluid reveals six different types. Thus, there is reason to be skeptical about the notion that the red blood cell is a single cell.

SUMMARY OF THE INVENTION

It is therefore a primary object of this invention to provide a method of categorizing and extracting red blood cells.

It is another object of this invention to find new functions of red blood cells which are greater parts of human blood.

A still more specific object of this invention is to provide methods for fractionating red blood cells into different functions, which method can be used for, among other things, such research.

In order to achieve the above objects, the inventor of the present invention has performed research on the concept of fractionating red blood cells of human blood into several fractions. The inventor found that the tested blood could be fractionated into three layers after the blood was combined with dextran and then maintained under a certain condition for a certain period. The fractionated blood cells contained in these three layers provided different functions on bacteria, respectively. The present invention is based on this knowledge.

The above described objects are accomplished by the method for fractionating red blood cells of human blood into three fractions according to the present invention which comprises the following steps: (a) a human blood sample is mixed with dextran aqueous solution and is kept stationary for 60 to 75 minutes to fractionate this blood sample into three layers; (b) these upper, intermediate, and lower layers are individually separated and collected; and (c) the upper layer sample is treated with a hypotonic solution for a short period and then combined with a hypertonic solution.

Further, the present invention may provide another method for producing a fraction including antibacterial red blood cells, which comprises the following steps: (a) a human blood sample is mixed with dextran aqueous solution and is kept stationary for 60 to 75 minutes to fractionate this blood sample into three layers; (b) the upper layer is separated from the other layers; and (c) the upper layer is treated with a hypotonic solution for a short period and then is combined with a hypertonic solution.

Furthermore, the present invention may provide still another method for producing a fraction including bacterial proliferation inhibitory red blood cells, which comprises the following steps: (a) a human blood sample is mixed with dextran aqueous solution and is kept stationary for 60 to 75 minutes to fractionate this blood sample into three layers; and (b) the intermediate layer sample is separated and collected from the other layers.

Accordingly, the methods provided by the present invention can easily fractionate three different blood fractions including red blood cells as a main component and having different functions. These three different fractions may be applied to several clinical tests such as antibacterial tests and the like.

The present invention also provides a method for fractionating red blood cells into three layers, each of which includes a different type of red blood cells. The red blood cells in the upper layer are the upper layer (UL) RC, those of the intermediate layer are the intermediate layer (IL) RC, and those of the lower layer are the lower layer (LL) RC.

These and other objects and many of the attendant advantages of this invention will be readily appreciated as the same becomes better understood by reference to the following detailed description when considered in connection with the accompanying drawing.

BRIEF DESCRIPTION OF THE DRAWINGS

FIG. 1 is a microscopic view of a mixture containing RPMI-1640 and a drop of blood from a patient's cubital vein.

FIG. 2 is a microscopic view of the mixture shown in FIG. 1, after twenty minutes of exposure to sunlight.

FIG. 3 is a microscopic view of the mixture shown in FIG. 1 after 3.5 hours

FIG. 4 is a microscopic view of the mixture shown in FIG. 1 after 24 hours.

FIG. 5 is a microscopic view of an unprocessed mixture of RPMI-1640 and a drop of blood from a patient's cubital vein, 24 hours old after mixing.

FIG. 6 is a microscopic view of a mixture containing synovial fluid which is extracted from patients with arthrosis deformans of the knee, rheumatoid arthritis, and the like, a drop of blood of the same type, and RPMI-1640.

FIG. 9 is a diagrammatic illustration of changes in the shape of red blood cells included in the fractions provided by the methods according to the present invention.

FIGS. 60 and 61 are graphs of the RC quantity with respect to time in samples containing muscle tissue.

FIGS. 62 and 63 are graphs of the RC quantity with respect to time in samples containing fat tissue FIGS. 64 and 65 are graphs of the RC quantity with respect to time in samples containing bone marrow.

FIG. 66 is a graph of the RC quantity with respect to time in samples containing cartilage tissue.

FIG. 71 is a microscopic view of white, shiny substances which resemble grains of rice in a solution obtained by mixing RPMI-1640 with one drop of blood taken from the cubital vein of a patient afflicted with articular rheumatism, anemia, or cancer.

FIG. 72 is a microscopic view of black spots into which the substances shown in FIG. 71 convert during intense action thereof.

FIG. 73 is a microscopic view of the substance illustrated in FIGS. 71 and 72 after its activity stops suddenly, and terminates in black spots.

FIGS. 74 and 75 are microscopic views of a mixture which was mixed according to the present invention, but which was treated with anti-coagulants.

FIG. 97 is a microscopic view of a sample taken from a liver cancer patient, the sample having been incubated for a period of 24–48 hours.

FIG. 98 is a microscopic view of a sample taken from a breast cancer patient, the sample having been incubated for a period of 24–48 hours.

FIGS. 99 and 100 are microscopic views after an initial incubation period, of a sample taken from a rheumatoid arthritis patient.

FIG. 101 is a microscopic view during a terminal period, showing masses of big yellow dust and rather small white dust in a sample taken from the rheumatoid arthritis patient.

FIGS. 120, 121 and 122 are microscopic views of the upper layer (UL), intermediate layer (IL), and lower layer (LL), respectively, of a sample taken from a Crohn's disease patient, after having been incubated for 4 hours.

FIGS. 123, 124 and 125 are microscopic views of the upper layer (UL), intermediate layer (IL), and lower layer (LL), respectively, of a sample taken from a Crohn's disease patient, after having been incubated for a period of 16 days.

FIGS. 132–142 are microscopic views of additional samples which were processed according to examples 1 and 2, wherein FIGS. 133, 134 and 135 are of the upper layer (UL), intermediate layer (IL), and lower layer (LL), respectively, from a patient afflicted with rheumatoid arthritis; FIGS. 136, 137 and 138 are of the upper layer (UL), intermediate layer (IL), and lower layer (LL), respectively, from a patient afflicted with colon cancer; FIGS. 139, 140 and 141 are of the upper layer (UL), intermediate layer (IL), and lower layer (LL), respectively, of a sample which was infected with bacteria and which was treated with an antibiotic; FIG. 139 is of a sample which permits no multiplication of the bacteria; FIG. 140 is of a sample wherein a minute amount of bacterial multiplication occurred, and FIG. 141 is of an overwhelming amount of bacterial multiplication.

FIGS. 142–149 are electron micrograms of the upper layer (UL) RC from a rheumatoid arthritis patient, taken after processing according to examples 1 and 2.

DETAILED DESCRIPTION OF THE PREFERRED EMBODIMENT

Figure 7:
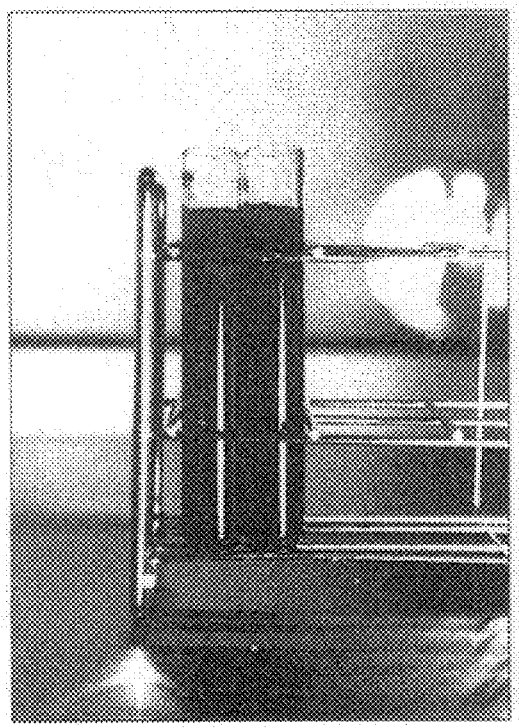
FIG. 7 is an elevation view of two test tubes which contain a mixture prepared according to the present invention immediately after its ingredients are mixed.

First, according to one preferred embodiment of the present invention, human blood (including all blood ingredients) is mixed with dextran aqueous solution (e.g., Dextran 70 which is commercially available from Tokyo kasei Chemical, of Tokyo, Japan). The dextran aqueous solution used in the present invention preferably is selected from 5 to 10 w/v% of dextran aqueous solution or physiological saline solution, more preferably 5 to 10 w/v% of dextran physiological saline solution, most preferably 5 to 8 w/v% of dextran physiological saline solution.

This dextran aqueous solution to be added into the blood sample is preferably one to twice the volume of the blood sample, more preferably 1.5 times. The mixture of the blood and the dextran aqueous solution is sufficiently stirred and then is kept stationary for 60 to 75 minutes. The mixture forms three layers (upper, intermediate, and lower layers). The layers are visually distinguishable from one another.

The upper layer is separated from the other layers by means of a pipette. The separated layer is treated with a hypotonic solution for a short period and then is combined with a hypertonic solution. Finally, one fraction containing red blood cells providing antibacterial activity is produced. In a practical manner, the upper layer is subjected to centrifugal separation to collect blood cells. The separated blood cell sample is further combined with a hypotonic solution, and after a short period, is combined with a hypertonic solution to provide an isotonic solution. In the present invention, a saponin solution preferably is used for the hypotonic solution, but any materials capable of making the hypotonic solution isotonic may be used as the hypertonic solution. Such short period for keeping the blood cell sample in the hypotonic solution preferably is about 30 seconds. If the treatment period in the hypotonic solution is significantly shorter, the produced sample will not be antibacterial. On the other hand, if the treatment period is significantly longer, hemolysis will excessively progress and thus the sample would include fewer red blood cells.

The intermediate and lower layers may be selectively taken from the separated layers by means of a pipette.

The three resulting red blood cell fractions then may be added to a liquid medium, such as RPMI-1640, MEM, BME, Ham F12, MCDB104, MCDB153, and the like, and can be applied to various research projects and studies, such as observations of their effects and actions on various bacteria.

One experiment wherein specific bacteria were inoculated onto the aforementioned hypotonic treated upper layer indicated that the red blood cells contained in the upper layer attacked these bacteria while the leukocytes contained in the upper layer did not act on these bacteria at all. In other words, the red blood cells contained in the upper layer provide an antibacterial function. The inhibit not only the movement of the bacteria but also their proliferation. When the same bacteria were inoculated onto the intermediate layer, proliferation of the bacteria was remarkably inhibited. When the lower layer was subjected to the similar experiment, this test resulted in no action on the inoculated bacteria.

According to another preferred embodiment of the present invention, the same three red blood cell fractions; the upper, intermediate and lower layers, were fractionated and prepared as liquid medium in the same manner as described above. An incubated leukocyte sample taken from another human blood was added into the upper and intermediate layers, respectively. In order to observe action on bacteria by these fractionated samples, specific bacteria were immediately added into the upper and intermediate layers including the incubated leukocytes, respectively. These samples were observed three times at intervals of 24 hours; i.e., after 24, 48, and 72 hours. These observations indicated that proliferation of bacteria was remarkably inhibited. Reference tests using commercially available antibiotics were carried out on the same occasion to compare with the above results according to the present invention. This comparison also proved that the upper and intermediate layer samples provided an inhibitory effect on bacteria which was superior to all antibiotics. The power to inhibit the proliferation of bacteria was 6 to 9 times greater when compared to commercially available antibiotics.

As is clear from these experimental tests, specific materials having an inhibitory effect on the proliferation of bacteria which is stronger than any existing antibiotics are generated in the liquid medium samples composed of the upper layer including red blood cells and incubated leukocytes added thereto, and the intermediate layer including red blood cells and incubated leukocytes added thereto, and further their activated condition is kept stable for a long period.

It should be understood that such inhibitory materials are either cell-products composed of the red blood cells contained in each layer and the leukocytes added thereto, or by-products secreted out of the blood cells. It should be understood that such by-products are the first type materials secreted out of the red blood cells in the upper or intermediate layer acted by the incubated leukocytes added thereto; the second type materials generated when the incubated leukocytes are broken or secreted out of the incubated leukocytes; or the third type materials generated by the cooperation between the red blood cells of each fraction and the incubated leukocytes. In order to specify such inhibitory materials, the cultured solution of the red blood cell fraction combined with the incubated leukocytes is subjected to analysis via filtering and extracting processes.

The present invention will be further understood by the following examples, though it is understood that the present invention is not limited to these examples.

EXAMPLE 1

The starting materials and equipment for this example include Dextran 70 (commercially available from Tokyo Kasei Co., Ltd of Tokyo Japan), saline solution (commercially available from Hishiyama Pharmaceutical, Osaka Japan), RLB (hypotonic solution commercially available from Harajuku Clinic, Tokyo Japan), BELMAR (hypertonic solution commercially available from Harajuku Clinic, Tokyo Japan), RPMI-1640 (liquid for tissue culturing which is commercially available from GIBCO BRL 11875-093 USA), Costar flask, a clean-bench, an incubator and fresh human blood.

While the RLB and BELMAR solutions are described in the preferred method, it is understood that other solutions having a half salinity concentration when compared to saline solution (i.e., isotonic sodium chloride solution) can be substituted for the RLB hypotonic solution and that other solutions having a double salinity concentration when compared to saline solution (i.e., isotonic sodium chloride solution) can be substituted for the BELMAR hypertonic solution.

Initially, 10 milliliters of the fresh human blood of a healthy person is combined with 15 milliliters of dextran solution (which was prepared by dissolving 7.0 g of Dextran 70 manufactured by Tokyo Kasei Co., Ltd in 100 ml of physiological saline solution). The resulting mixture is stirred using a pipette, and is then kept stationary for 60 to 75 minutes. The stationary mixture initially appears as shown in FIG. 7.

Figure 8:
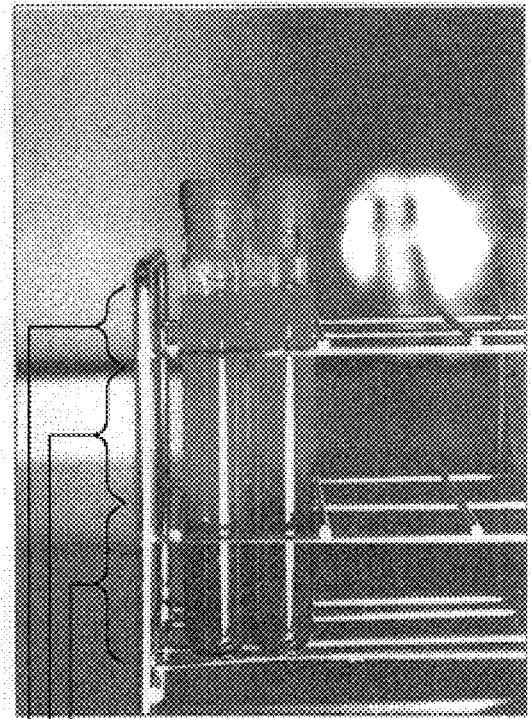
FIG. 8 is an elevation view of the two test tubes shown in FIG. 7 after the mixture is kept stationary for 60 to 75 minutes and the mixture has separated into three visually distinct layer.

During the 60 to 75 minutes, however, three visually distinct layers become readily apparent in the mixture. The three visually distinct layers are shown in FIG. 8 and include an upper layer (UL), an intermediate layer (IL), and a lower layer (LL).

The upper layer (UL) is first sampled using a pipette. The collected sample contains red cells (RC), as well as abundant white cells (WC). This collected sample from the upper layer (UL) then is subjected to a centrifugal separation to precipitate blood cells (red blood cells and leukocytes) and to provide a clear layer of liquid above the precipitate. The clear layer of liquid is discarded. The precipitated part, however, is combined with 30 milliliters of a hypotonic solution (e.g., RLB, produced by Harajuku Clinic). Thirty seconds after the hypotonic solution is added, the resulting solution is combined with 10 milliliters of a hypertonic solution (e.g., BELMAR, produced by Harajuku Clinic). This mixture then is subjected to a centrifugal separation to collect blood cells. In particular, the clear liquid which appears above the blood cells as a result of centrifugation is discarded, while the precipitated cells are retained. The precipitated cells then are combined with 3 milliliters of a liquid medium (e.g., RPMI-1640). The resulting solution then is poured into a Costar flask and will be referred to hereinafter as "sample A".

In addition to the taking of sample A, four drops of the intermediate layer (UL) are extracted from the three layer solution using a pipette. This drop-solution is combined with 3 milliliters of liquid medium (RPMI-1640). The resulting solution is referred to as "sample B".

A drop from the lower layer (LL) also is extracted using a pipette. This drop-solution is combined with 3 milliliters of liquid medium (RPMI-1640) 3 ml. The resulting solution is referred to as "sample C".

TEST AND RESULTS FOR EXAMPLE 1

A small amount of *Pseudomonas aeruginosa* was inoculated into the samples A, B, C and RPMI-1640 (as a control sample), respectively. These samples were kept for 5 to 6 hours at room temperature, and then incubated under the condition of 5% $CO_2$, 37° C. The resulting samples A, B, C, and the control sample were observed through a microscope to determine the action of the samples A, B, C and the control sample on the inoculated bacteria.

The microscopic observation revealed that the sample A included some leukocytes in addition to red blood cells, and the red blood cells were changed into various shapes as shown in 9. According to the observation of the sample A incubated for six hours, the leukocytes did not positively act on the inoculated bacteria at all, while the red blood cells changed in their shapes moved toward the inoculated bacteria and thus the bacteria were prohibited from moving freely.

The microscopic observation resulted in that the sample B also included a small amount of leukocytes in addition to red blood cells, and the red blood cells were changed into various shapes as shown in FIG. 9. According to the observation of the sample B incubated for six hours, the inoculated bacteria were remarkably decreased in comparison with the control sample.

According to the microscopic observation of the sample C, the sample C included only red blood cells which were changed into various shapes. The counted number of the inoculated bacteria in the sample C were substantially equal to that of the control sample.

EXAMPLE 2

According to a second example of the present invention, the three visually distinct layers shown in FIG. 8 are generated in the manner described above. Another sample A is taken in the same manner as described above.

In addition, a sample D is provided by extracting 4 to 6 drops from the upper layer (UL) using a pipette and combining the extracted drops with 3 milliliters of RPMI-1640.

Another sample, defined as sample E, is provided by extracting 4 to 6 drops from the intermediate layer (IL) and combining the extracted drops with 3 milliliters of RPMI-1640.

Still another sample, defined as sample F, is provided by extracting ½ to 1 drop from the lower layer (LL) and combining the extracted solution with 3 milliliters of RPMI-1640.

The samples A, D, E, and F then are contaminated with pseudomonas sp. using an injection needle tip (a small amount of bacteria). The sample A is left at room temperature (e.g., 15–23° C.) for 5 to 6 hours and then is cultured in the 37° C. and 5% $CO_2$ incubator.

Next the sample A is contaminated with 0.1 milliliter of RPMI-1640 having a large number of pseudomonas sp. bacteria.

The samples then are regularly observed using a scanning microscope (e.g., a Nikon TMS-F MFA 20100 microscope).

Samples A and D to F are contaminated with pseudomonas sp. using an injection needle tip (a small amount of bacteria). The samples are left at room temperature (e.g., 15 to 23° C.) for 5 to 6 hours and then are cultured in the 37° C., 5% $CO_2$ incubator.

The sample A then is contaminated with 0.1 milliliter of RPMI-1640 having a large number of pseudomonas sp bacteria.

The samples then are regularly observed using a scanning microscope.

RESULTS OF EXAMPLE 2

The results of example 2 include the classification of red blood cells (RC) into at least three different groups, namely, those found in the upper layer (UL), the intermediate layer (IL), and the lower layer (LL).

Figure 10:
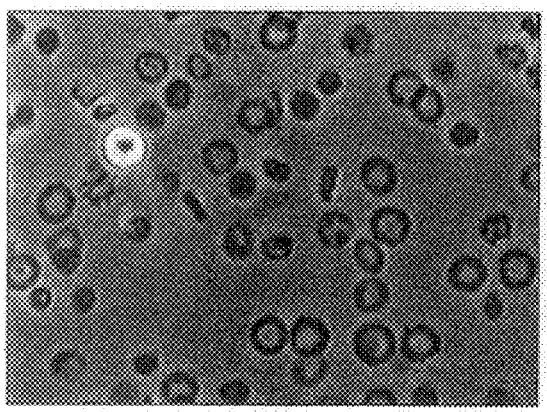
FIGS. 10–12 are microscopic views of an upper layer (UL) sample containing different types of RC-derived cells, obtained according to the present invention.
Figure 11:
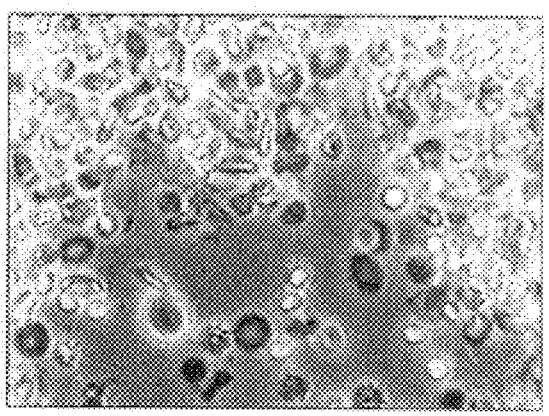
Figure 12:
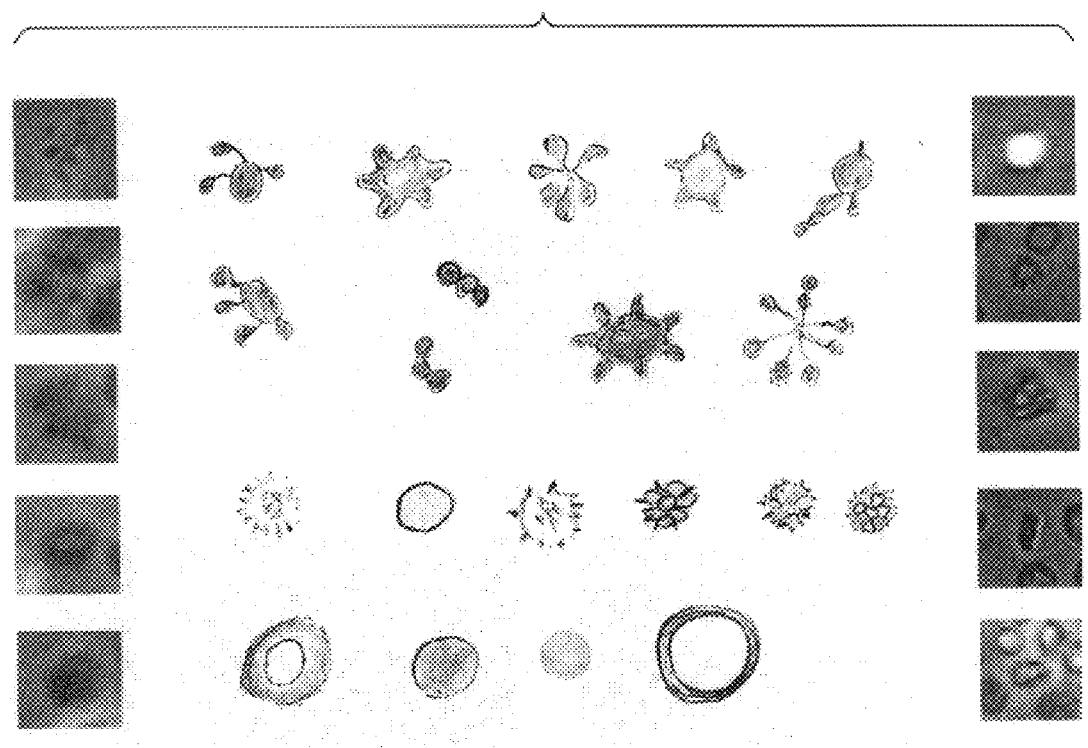

Many different types of RC-derived cells, as shown in FIGS. 10–12, are observed in the group taken from the upper layer (UL). When these are exposed to pseudomonas sp., the RC and RC-derived cells from the upper layer (UL) demonstrate frenzy-like movement, rotating on and around pseudomonas sp. This movement should be interpreted as their bacterio-static influence. RC and RC-derived cells continue this movement even after pseudomonas sp. ceases its own movement, as if to prevent resurrection of the pseudomonas sp.

Figure 13:
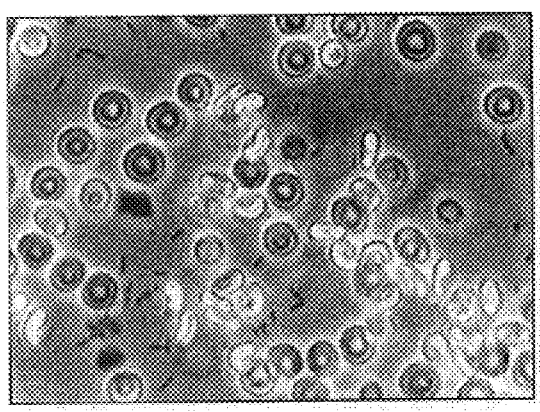
FIG. 13 is a microscopic view of an intermediate layer (IL) sample obtained according to the present invention, wherein multiplication of pseudomonas sp. is suppressed.

The RC in the intermediate layer (IL), as shown in FIG. 13, are static but survive much longer than the others. The multiplication of pseudomonas sp. is suppressed in the case of the intermediate layer (IL).

Figure 14:
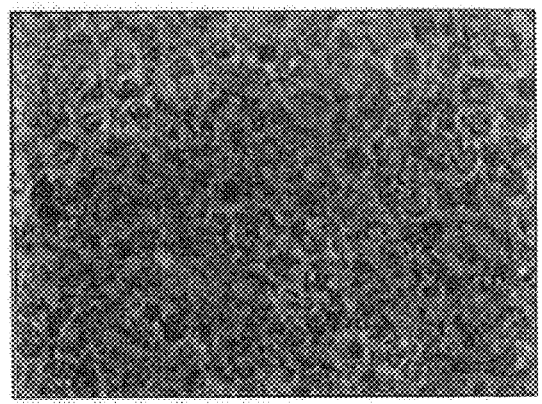
FIG. 14 is a microscopic view of the RC in a lower layer (LL) obtained according to the present invention, wherein multiplication of the pseudomonas sp. is very fast.

The RC in the lower layer (LL), as shown in FIG. 14, fail to demonstrate the aforementioned movement and instead remain static. Multiplication of the pseudomonas sp. in the lower layer (LL), in contrast to the other layers, is very fast.

Figure 15:
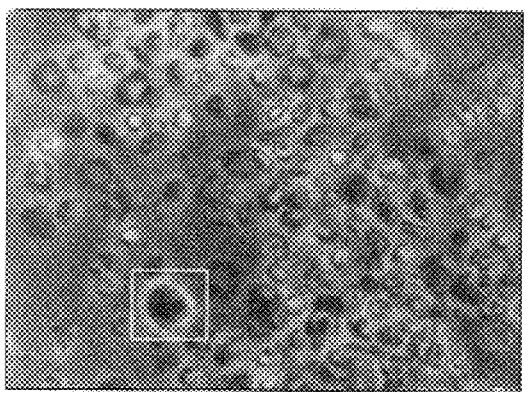
FIG. 15 is a microscopic view of RC and RC-derived cells from the upper layer (UL), wherein pseudomonas sp. eventually sticks to a cell that demonstrates active rotative movement.

The movement of the RC and RC-derived cells from the upper layer (UL) according to Examiner 2 has been observed and videotaped. As shown in FIG. 15 position A in the upper frame), pseudomonas sp. eventually sticks to a cell that demonstrates active rotative movement. A leukocyte in FIG. 15 is shown in the square box.

Figure 16:
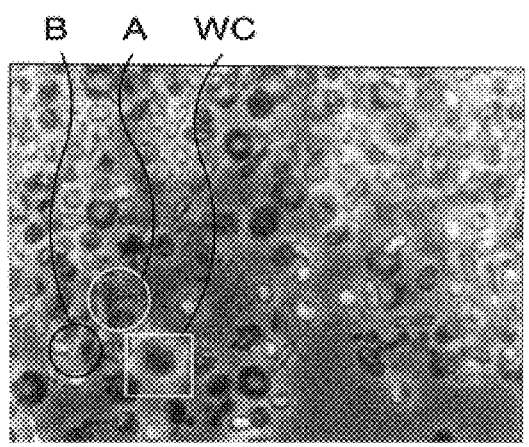
FIGS. 16–18 are microscopic views of many RC cells taken while the RC cells repeat an incessant aggressive attack against pseudomonas sp.
Figure 17:
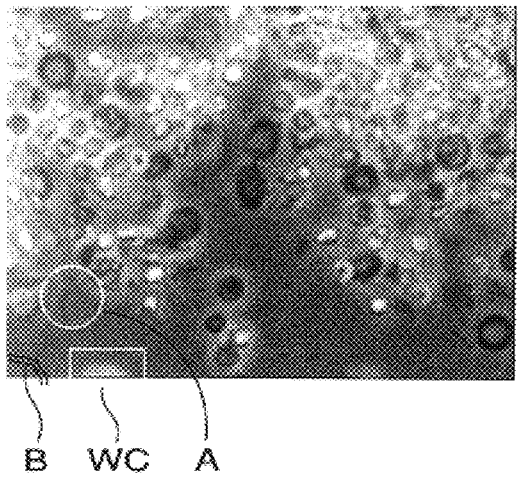
Figure 18:
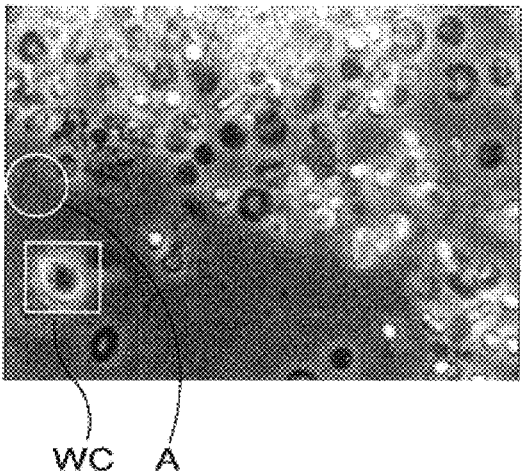
Figure 19:
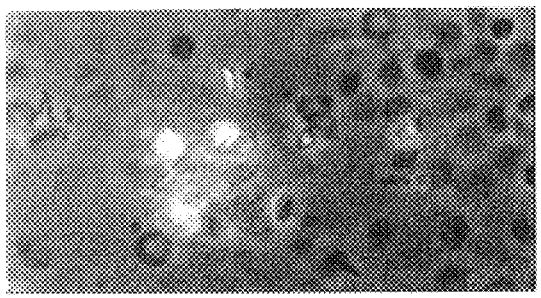
FIGS. 19–22 are microscopic views of five leukocytes.
Figure 20:
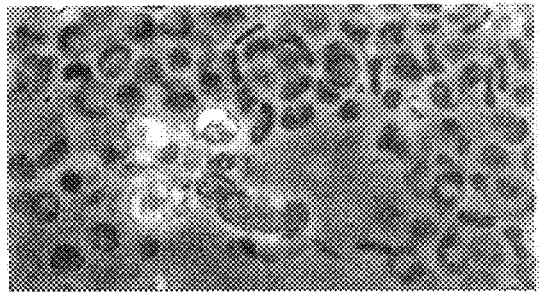
Figure 21:
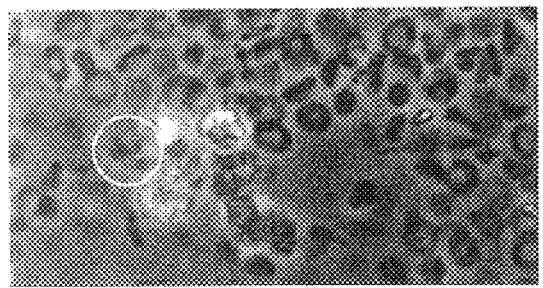
Figure 22:
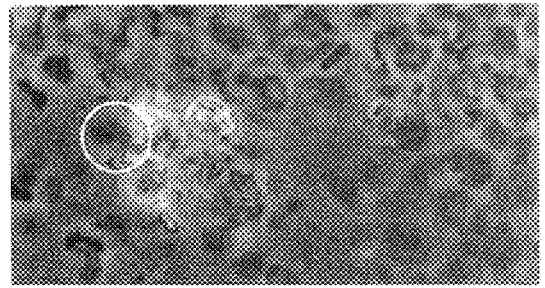
Figure 23:
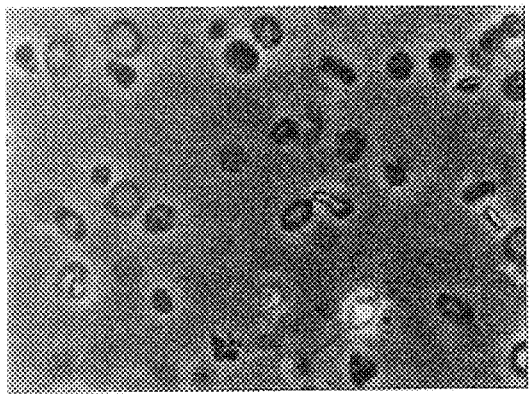
FIGS. 23–26 are microscopic views of erythrocytes which transform into cells with various types of complex shapes when left free of pseudomonas sp.
Figure 24:
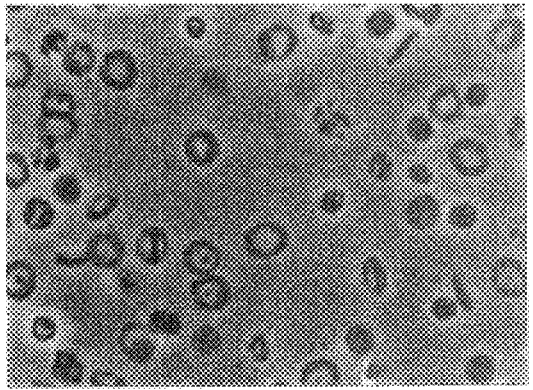
Figure 25:
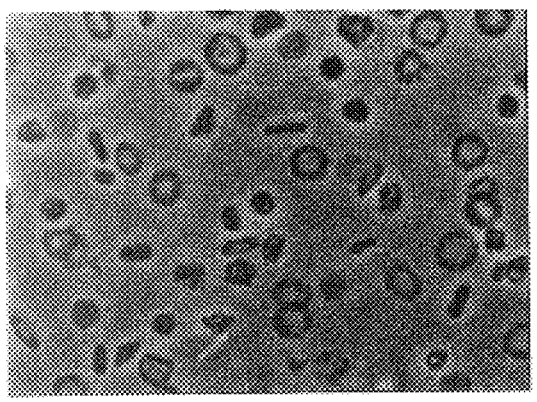
Figure 26:
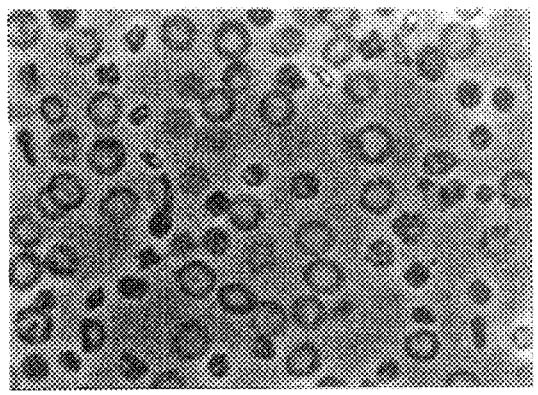

As shown in FIGS. 16–18, it is as though many RC cells repeat an incessant aggressive attack against pseudomonas sp. Pseudomonas sp., as a result, ceases its movement after about 1 minute and 45 seconds. After 2 minutes, another pseudomonas sp. is stuck to the bottom in position B, and RC and RC-derived cells demonstrate similar repetitive aggressive movement. The movement resembles a "dancing butterfly but attacking as a bee". During an observation time of almost 2 hours, these two pseudomonas sp. never regained their movement.

FIGS. 19–22 show five leukocytes slightly toward the left in the Figures. One of the leukocytes exhibits amebic movement. The black double-ring cells around the leukocytes are the red blood cells, and the black spots or bars are the bacteria.

During incubation of the pseudomonas sp., when they proliferate to the maximum point, they gradually turn into a grainy shape and lose the bar-like shape. If the bacteria in this state (pseudomonas sp.) is added to RPMI-1640 where hemocytees are being incubated, they will gradually develop their bar shapes again.

The cell which performs amebic movements moves actively in the direction of the two pseudomonas sp. in the right bottom part of the Figures. This scene shown in the Figures changes gradually, but the amebic movement continues. One of the pseudomonas sp. is attached on top of the leukocyte to its left, and begins to make active movements. The leukocyte that exhibited the amebic movement approaches very closely to the two pseudomonas sp., but does not show any sign of phagocytosis. On the left side of the group of leukocytes, three pseudomonas sp. have attached and started to make active movements. In the center, also, one has attached. While the red blood cells fight against these pseudomonas sp. as shown in FIGS. 15–18, the leukocytes fail to perform phagocytosis.

If, however, the erythrocyte is left alone, without injecting pseudomonas sp., it transforms into cells with various types of complex shapes, as shown in FIGS. 23–26. Some of the shapes are similar to the shapes which appear in FIGS. 15–18. As indicated above in the description of sample A, the erythrocyte can be transformed by putting it in the hypotonic solution RLB for 3 seconds, then adding to it the hypertonic solution to prepare an osmotonic solution, in order to culture erythrocyte. The reason for such processing relates to the edema which typically occurs at the site of infection. The edema means that the site of infection is in a state of hypotonic solution. In order to observe erythrocyte at the site of infection, the erythrocyte is exposed to a hypotonic solution. As a result, the erythrocyte is transformed. Hereinafter, the erythrocyte which exists before this transformation or metamorphosis will be referred to as the "masked erythrocyte". The erythrocyte after metamorphosis will be referred to as "the RC-derived cell."

Quite possibly the creatures living in ancient times may have had erythrocytes of such various forms which evolved along with man to the current state and which developed into having their present shapes. The "masked erythrocyte" is considered to be the present form of UL erythrocyte.

Figure 27:
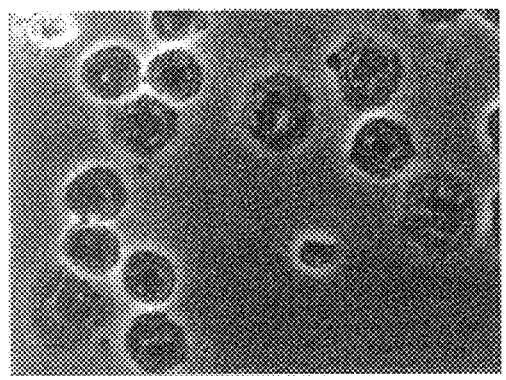
FIG. 27 is a microscopic view of carnival cells obtained by processing white blood cells according to the present invention.

If white blood cells, by contrast, are extracted and if purely white cells alone are incubated, they will assume the kind of shape shown in FIG. 27. These are referred to as "carnival cells" because they resemble a gathering of excited people around a float at a carnival. Several creatures, presumably mitochondria, can be observed moving actively around the core.

Figure 28:
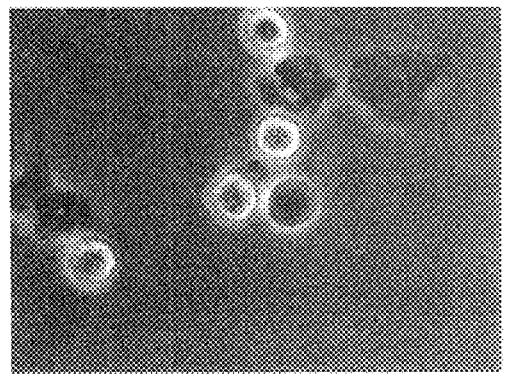
FIG. 28 is a microscopic view of leukocytes which gradually assume a caterpillar shape.
Figure 29:
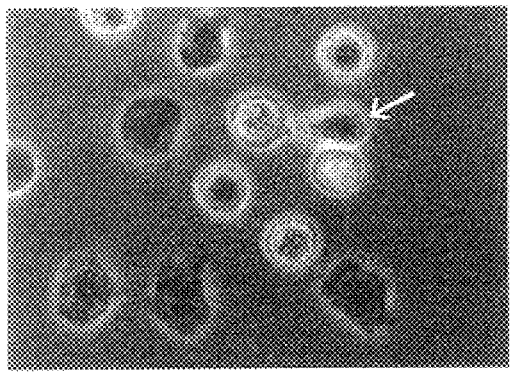
Figure 30:
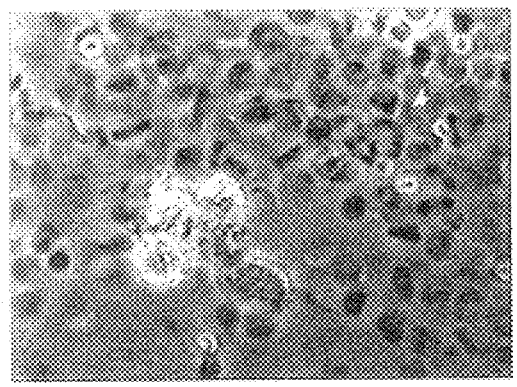
FIG. 30 is a microscopic view of cells which exhibit amebic movements.
Figure 31:
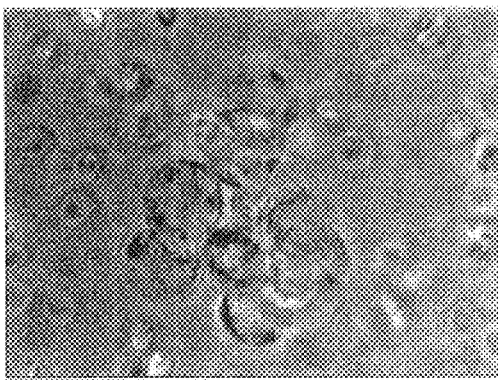
FIG. 31 is a microscopic view of white blood cells that assume balloon-like shapes.

As shown in FIG. 28, some cells do not change at all. Some leukocytes therefore remain unchanged and others gradually assume a caterpillar shape, as shown in FIG. 29. In addition, a small number of cells, shown in FIG. 30, exhibit amebic movements similar to that of FIGS. 19–22. As shown in FIG. 31, there also are white blood cells that assume balloon-like shapes.

Of the various results shown in FIGS. 27–31, the largest in number is the carnival cell; the second largest in number is the balloon-like shape; and the third largest in number is the unchanging type. The smallest in number is the amebic type. The following chart generally indicates the relative frequency of occurrence for each type of incubated white blood cell. Each "+" in the chart denotes the occurrence of several cells of the indicated type:

| Type of Incubated White Blood Cell | Frequency |
| --- | --- |
| Balloon type of white blood cell | +++ to ++ |
| Amoeba type of white blood cells | + |
| Carnival type of white blood cells | ++++ |
| Unchanging type of white blood cells | +++ to ++ |
| Caterpillar type of white blood cells | ++ to +++ |

As indicated above, phagocytosis has not been proven. Metchnikoff's publication around 1884 regarding phagocytosis was probably based on experiments in which micrococcus, such as staphylococcus and chain coccus, were introduced while incubating the white blood cells, and where the incubated white blood cells were extracted and placed on a glass, were dried and dyed, and then were observed through a microscope. Using such a procedure, the round grain inside the white blood cell and the bacteria around it probably looked the same. This, in turn, may have led to a mis-observation, the result of which was an erroneous conclusion that phagocytosis had occurred.

The upper layer (UL) red blood cells make the bacteria lose its biological activity and tranquilizes them. After the bacteria become still, they presumably would be dissolved. Dr. Flemming, a Nobel laureate involved in the discovery of penicillin, has already reported that lyzozyrne chloride dissolves bacteria. It has been reported that while he was doing experiments, he sneezed, having a cold, and found then that bacteria did not grow in one part of the blood agar plate. The bacteria was dissolved and had disappeared. He examined this and discovered that the lyzozyme chloride discharged at the time of the sneeze dissolved the bacteria. This demonstrates that there are still many unknown enzymes in the human body besides lyzozyme chloride, and that they are dissolving bacteria. This may be part of what is characterized as the "natural healing power".

The resistance against bacteria of the type provided by the upper layer (UL) red blood cells and the intermediate layer (IL) red blood cells probably contributes to the natural healing power. Isolation of the upper layer (UL) and intermediate layer (IL) therefore provides an avenue into research on and use of the natural healing power.

Figure 32:
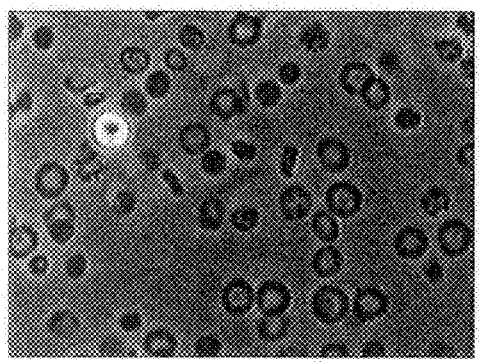
FIG. 32 is a microscopic view of the upper layer (UL) when the number of bacteria added thereto is relatively small.
Figure 33:
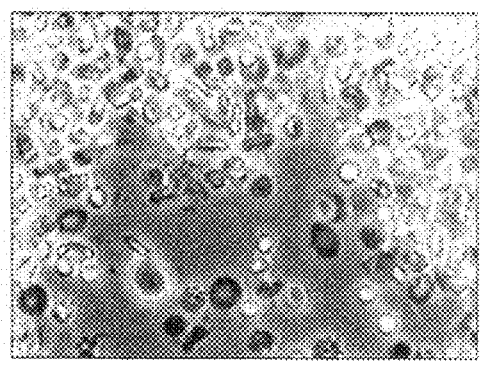
FIG. 33 is a microscopic view of the upper layer (UL) when 0.1 milliliter of RPMI-1640 containing numerous bacteria is introduced into the upper layer (UL) red blood cells.

The battle which was described above with reference to FIGS. 15–18 occurs when the number of bacteria exceeds a certain amount, after a very small amount of bacteria are contaminated and incubated in a 5% $CO_2$ 37° C. incubator for 6 to 8 hours. When the number of bacteria remains small, as shown in FIG. 32, no battle occurs between the bacteria and the upper layer (UL) red blood cells. However, when 0.1 milliliter of RPMI-1640 containing numerous bacteria is introduced into the upper layer (UL) red blood cells, a furious battle commences about 10 minutes after contamination. The battle takes place between the upper layer (UL) red blood cells and the bacteria throughout the entire scene represented by FIG. 33.

Based upon the activity which was observed in the scenes depicted by FIGS. 15–18, 32 and 33, it would appear that the human body is not aseptic as has been traditionally believed, but rather that a certain amount of bacteria exists and is drifting along in the human body. When there is a balance with the upper layer (UL) red blood cells/intermediate layer (IL) red blood cells, inflammation does not occur. This balance hereinafter is referred to as "the host-bacterial balance" or (HBB), though it is understood that it actually represents a host-bacterial cohabitational balance.

When in-motion observations of the scenes depicted in FIGS. 15–33 are made, certain conclusions can be drawn.

With regard to the subject matter illustrated in FIGS. 15–18, the RC and RC-derived cells demonstrate rotating or reversive movement on or around pseudomonas sp. This movement demonstrates the RC' bacterio-static action against pseudomonas sp. Possibly, the RC cells emanate some bacterio-static substance through this movement. RC and RC-derived cells repeat this movement as if to prevent resurrection of pseudomonas sp. even after pseudomonas sp. ceases its movement. The white cells are not active against pseudomonas sp.

With regard to the subject matter shown in FIGS. 19–22, it can be concluded that leukocytes demonstrate amoeboid movement but do not absorb bacteria into themselves (i.e., there is no phagocytosis); RC and RC-derived cells and pseudomonas sp. demonstrate similar movement as was observed in the scenes depicted in FIGS. 15–18; and leucocytosis means enhancement of RC functions (significans of leucocytosis) and no direct attack against bacteria.

With regard to the subject matter shown in FIGS. 23–26, it can be concluded that RC is not a single cell, but rather an upper layer (UL) red blood cell (i.e., a masked RC which possibly is genetically primitive), an intermediate layer (IL) red blood cell (i.e., a non-masked RC(IL) which possibly is genetically newer), and a lower layer (LL) red blood cell (i.e., a non-masked RC(LL) which possibly is genetically the newest).

Figure 34:
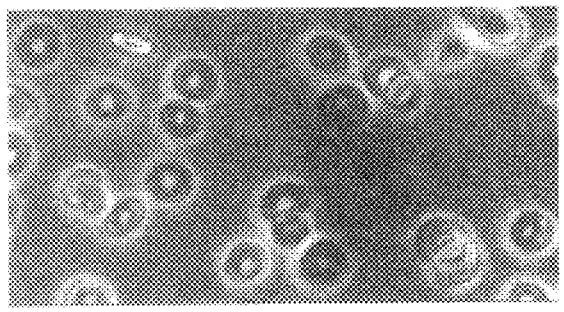
FIG. 34 is a microscopic view of normal upper layer (UL) RC.
Figure 35:
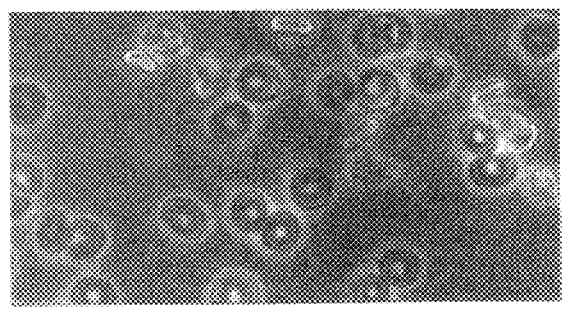
FIG. 35 is a microscopic view of normal intermediate layer (IL) RC.
Figure 36:
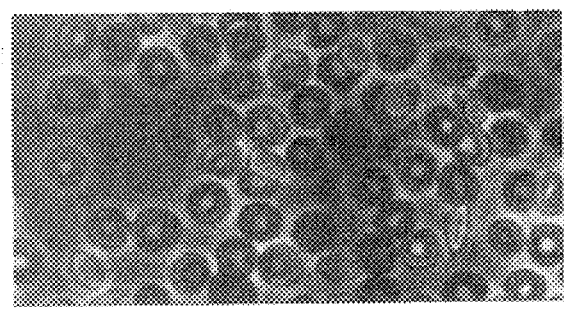
FIG. 36 is a microscopic view of normal lower layer (LL) RC.
Figure 37:
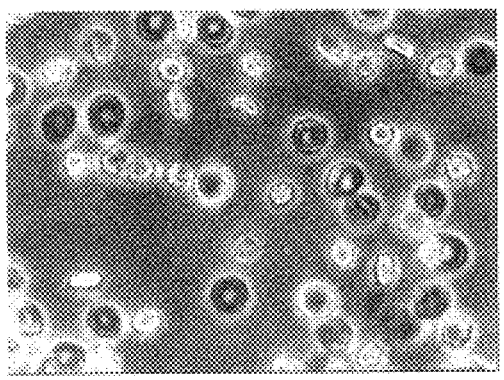
FIGS. 37–40 are microscopic views of the upper layer (UL) RC and intermediate layer (IL) RC which strongly suppress the proliferation of pseudomonas sp.
Figure 38:
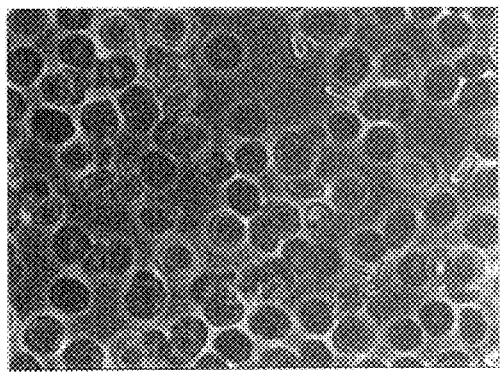
Figure 39:
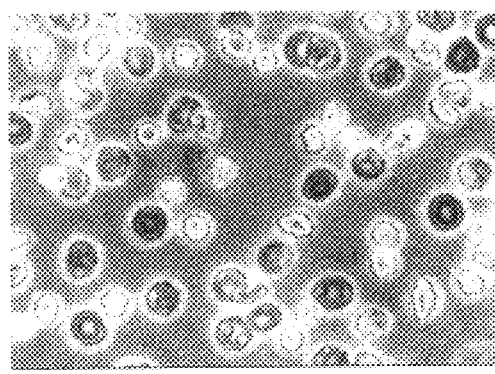
Figure 40:
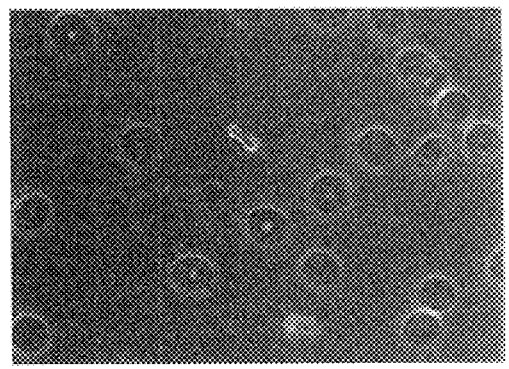

Normal upper layer (UL) RC, intermediate layer (IL) RC, and lower layer (LL) RC are shown in FIGS. 34–36, respectively.

The foregoing also suggests that living tissue normally contains a small amount of bacteria. This is contrary to the traditional theory that living tissue is aseptic. When tissue remains balanced with a permissible quantity of bacteria, it shows no sign of tissue inflammation. The inflammation occurs when this balance is broken, for example, because of general factors such as immuno-imbalance (e.g., due to influenza, hepatitis, excessive fatigue, malnutrition and many other diseases) or local factors such as bleeding, ischaemia, trauma, and the like. Exemplary forms of inflammation include that which is associated with myositis p., osteomyelitis p., arthritis purulenta, appendicitis, brain abscess, kidney abscess, liver abscess, and the like.

Figure 41:
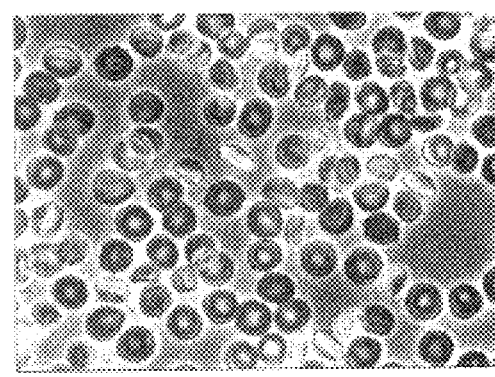
FIGS. 41 and 42 are microscopic views of the lower layer (LL) RC which has no power to suppress the proliferation of pseudomonas sp.
Figure 42:
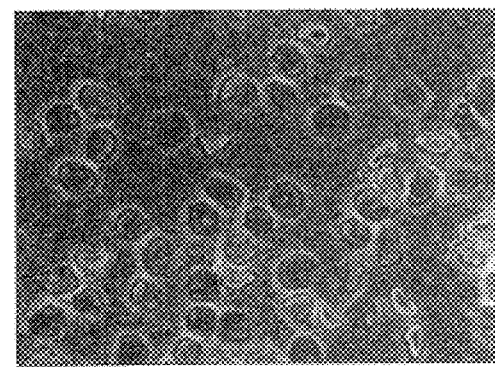
Figure 43:
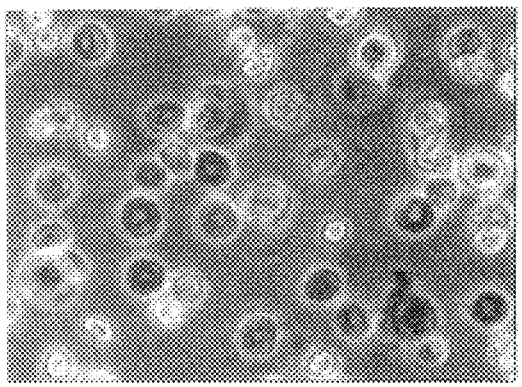
FIGS. 43–46 are microscopic views of the upper layer (UL) RC and intermediate layer (IL) RC which are incubated with leukocytes and exhibit a very strong function against pseudomonas sp.
Figure 44:
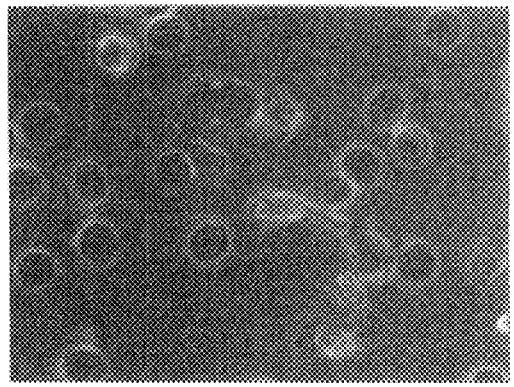
Figure 45:
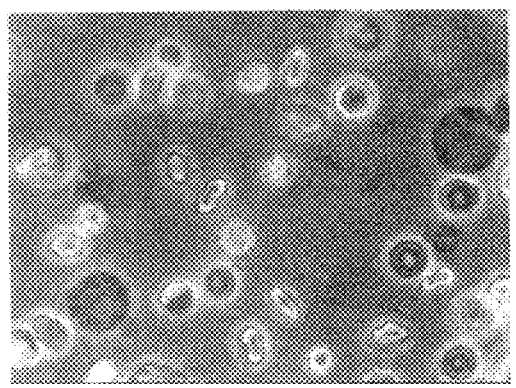
Figure 46:
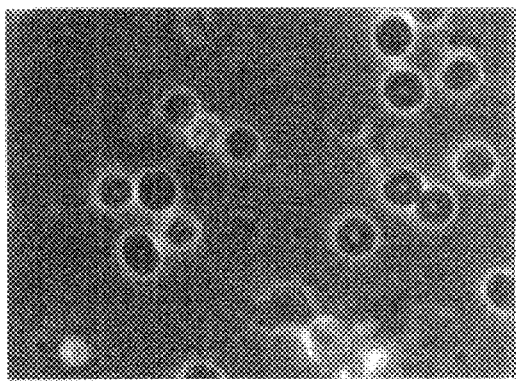

MIC therefore is not correct. The host bacterial balance mechanism is better. The upper layer (UL) RC and intermediate layer (IL) RC strongly suppress the proliferation of pseudomonas sp., as shown in FIGS. 37–40. The lower layer (LL) RC, however, has no power to suppress the proliferation of pseudomonas sp., as shown in FIGS. 41 and 42. The upper layer (UL) RC and intermediate layer (IL) RC incubated with antibiotics more strongly suppress the proliferation of the pseudomonas sp. The lower layer (LL) RC incubated with antibiotics does not suppress the proliferation of pseudomonas sp. Antibiotics suppress the proliferation of pseudomonas sp. with cooperation from the upper layer (UL) RC and intermediate layer (IL). MIC completely neglect the functions of the upper layer (UL) RC and intermediate layer (IL) RC against pseudomonas sp. bacteria. MIC therefore is not correct in clinical medicine. The function that the upper layer (UL) RC and intermediate layer (IL) RC suppress the proliferation of pseudomonas sp. is HBB.

FIGS. 43–54 show effective factors of HBB. As shown in FIGS. 43–46, the upper layer (UL) RC and intermediate layer (IL) RC exhibit a very strong function against pseudomonas sp. when they are incubated with leukocytes. As shown in FIGS. 47–50, the upper layer (UL) RC and intermediate layer (IL) RC also show the strong function against pseudomonas sp. when they are incubated with antibiotics, but it was weaker than with leukocytes.

Figure 53:
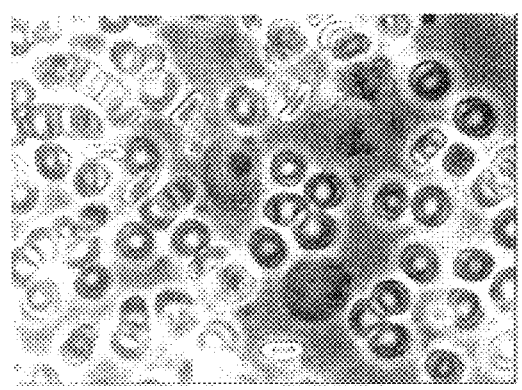
FIGS. 53 and 54 are microscopic views of the lower layer (LL) RC when incubated with iL.
Figure 54:
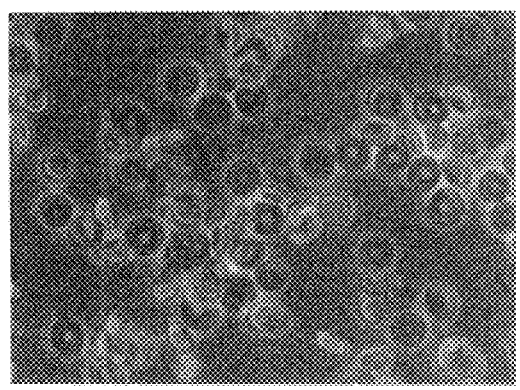
Figure 47:
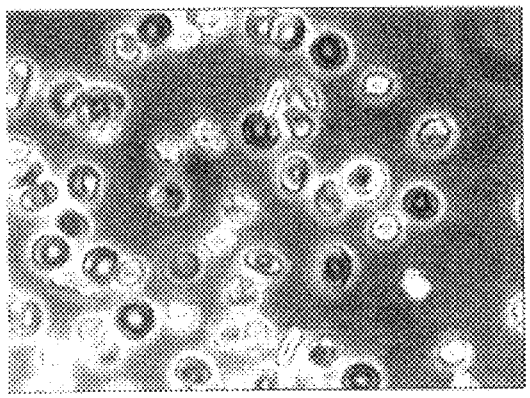
FIGS. 47–50 are microscopic views of the upper layer (UL) RC and intermediate layer (IL) RC which are incubated with antibiotics.
Figure 48:
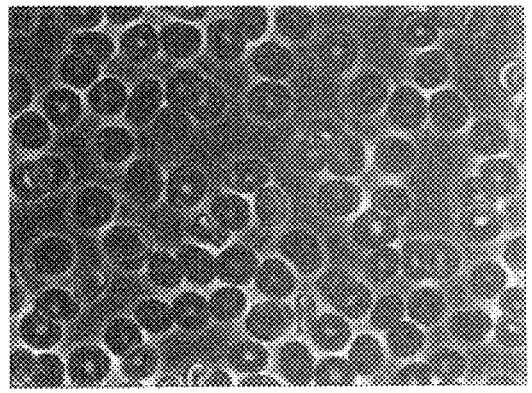
Figure 49:
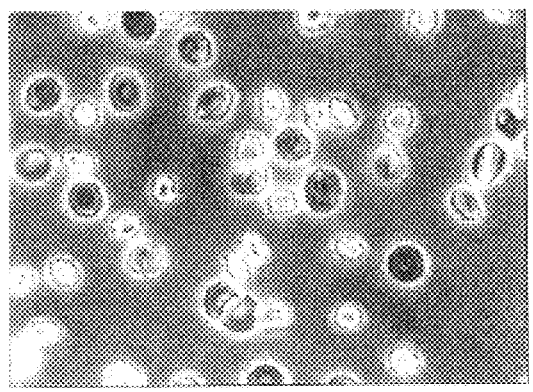
Figure 50:
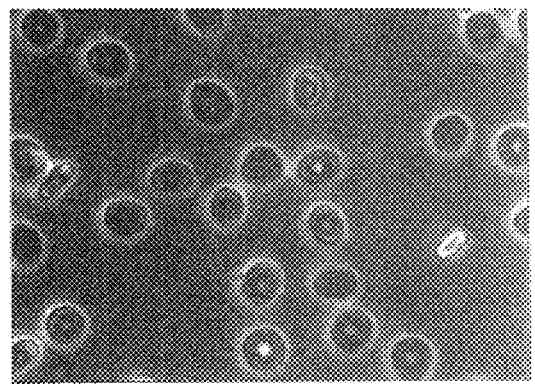
Figure 51:
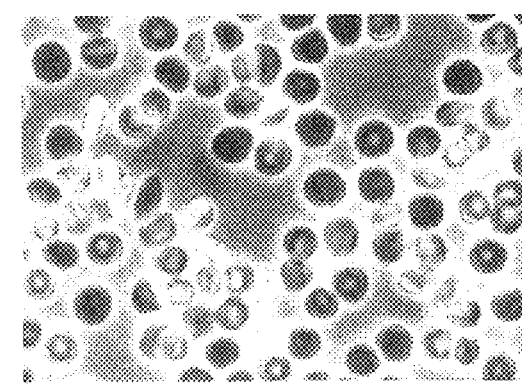
FIGS. 51 and 52 are microscopic views of the lower layer (LL) RC when cultivated with antibiotics, as shown in FIGS. 51 and 52.
Figure 52:
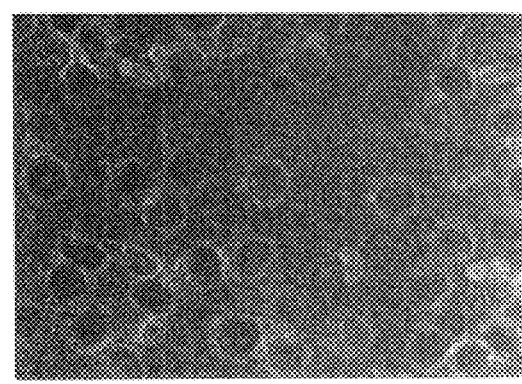

The lower layer (LL) RC provides no function to prevent the proliferation of pseudomonas sp. even when it is cultivated with antibiotics, as shown in FIGS. 51 and 52. As shown in FIGS. 53 and 54, even when the lower layer (LL) RC is incubated with iL, it has little power to suppress the proliferation of pseudomonas sp.

An effective factor of HBB therefore is an HBB mechanism based on upper layer (UL) RC and intermediate layer (IL) RC.

In view of the HBB mechanism, MRSA is not terrible. Living human tissue and the human body are not aseptic. Small amounts of bacteria coexist in the human body under HBB. There is, in this regard, coexistence and coprosperity between the tissue and the bacteria.

If a patient receives too much antibiotic(s), the bacteria is eliminated in the patient and the body itself cannot survive. The bacteria therefore change into MRSA in cooperation with the human body. Proliferation of upper layer (UL) RC and intermediate layer (IL) RC or emphasis of their function is most effective for MRSA. It is not the MRSA that is problematic, but rather the physicians who recklessly use antibiotics in large quantities to the extent that MRSA is produced.

Paradoxically, patients who have MRSA are those who still possess strength, while those patients who no longer have the strength to produce MRSA die. It should be understood that MRSA was produced by a joint effort between the human body and bacteria. Stronger antibiotics to kill these MRSA will end up being more toxic and will probably have stronger adverse reactions. The present invention provides an alternate course of action wherein the power of leukocytes is utilized and efforts are directed to increasing upper layer (UL) RC and intermediate layer (IL) RC or strengthening the functions of the living upper layer (UL) RC and intermediate layer (IL) RC.

Figure 55:
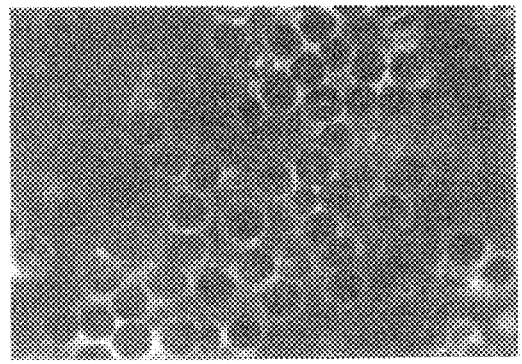
FIGS. 55 and 56 are microscopic views of the upper layer (UL) RC and the intermediate layer (IL) RC, after 5 days of incubation, when treated with antibiotics and exposed to small and thin bacteria which are very different from pseudomonas sp.
Figure 56:
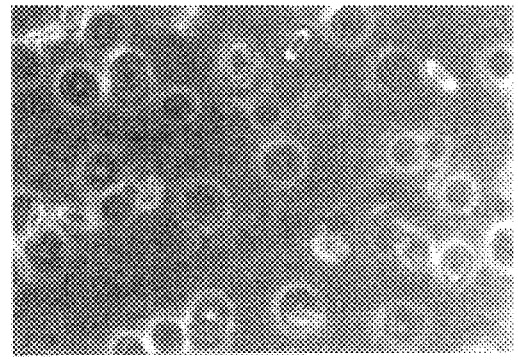

The results achieved by the present invention also indicate that antibiotics are not necessarily safe. Antibiotics in the upper layer (UL) RC and in the intermediate layer (IL) RC are effective at preventing proliferation of pseudomonas sp., but small and thin bacteria which are very different from pseudomonas sp. proliferate after 5 days of incubation, as shown in FIGS. 55 and 56. This proves the function of antibiotics and also proves the side effect of antibiotics on the bacteria. Moreover, oligospermia in adolescent males may be caused by antibiotics.

The following antibiotics have been used in the foregoing procedure:

| Chemical Name of Antibiotic |
| --- |
| cefapirin sodium |
| cefmiox sodium |
| cefalotin sodium |
| cefazoran dihydrochloride |
| cefatiam dihydrochloride |
| cefmetazole sodium |
| ceftazidime |
| cefsulodin sodium |
| cefepime dihydrochloride |
| subactam 1:cefoprazone 1 |
| piperacillin sodium |
| suitamicillin tosilate |
| aspoxicillin |
| ampicillin |

In the case of 0.5 gram per day:
  50 milliliters:5 milligrams=3 milliliters:X  X=15/50 X=0.3 milligram.
In the case of 1 gram per day:
  0.3 milligram×2=0.6 milligram.

Erythropoesis

The results achieved by the present invention can be applied to the erythropoesis of blood cells. It is a common belief that the blood cells are generated from the stem cells of the bone marrow. Anemia, however, is not observed among the elderly who suffer from the yellow bone marrow syndrome. In addition, the cause of sportsman's anemia is not known, neither is its self-healing process which commences when the athlete stops training. There is consequently doubt about the authenticity of this bone marrow erythropoesis, and it is surmised that the blood could also be generated from cells other than those in the stem cells of the bone marrow.

Figure 57:
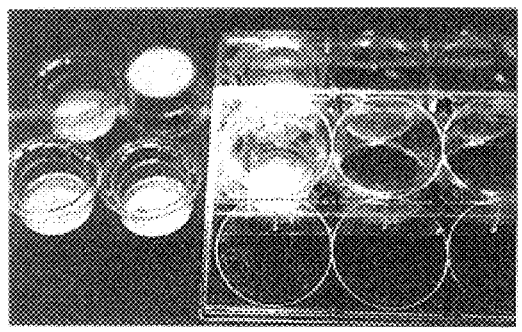
FIG. 57 is a perspective view of a Costar transwell.
Figure 58:
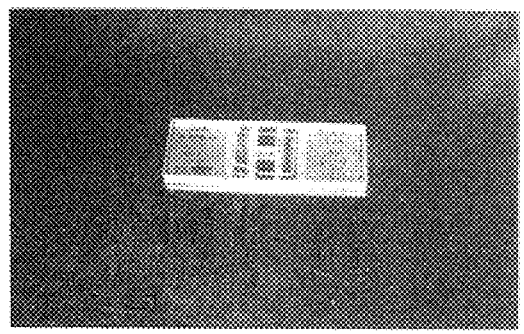
FIG. 58 is a perspective view of a Burker-Turk device.

In applying the results of the present invention to research on erythropoesis of the blood cells, the following equipment and materials are preferred:
  1. Costar transwell (e.g., Part No. 3412 from Costar's catalog, as shown in FIG. 57);
  2. Costar flask (e.g., Part No. 3056 from Costar's catalog);
  3. Pasteur pipettes which are sterilized;
  4. Tweezers which are sterilized;
  5. Scissors which are sterilized;
  6. Burker-Turk (as shown in FIG. 58);
  7. Clean-Bench (JNS-8AST);
  8. 5% $CO_2$ water-jacketed incubator (NS-502);
  9. Scanning microscope;
  10. RPMI-1640 (e.g., from GIBCO BRL, 11875-093).

According to a preferred method, tissues from muscle, fat, bone marrow, and cartilage are cultured using the Costar transwell. Preferably, the Costar transwell holds a very thin filter with pore holes of 0.4 micrometers. The inner part of the Costar transwell is filled with the sample tissue cells and RPMI-1640. The outer part is filled with blood of the same type as the tissue donor, together with RPMI-1640. The hourly quantitative changes of the RC cells then are recorded.

More specifically, the Costar flask is filled with 24 milliliters of RPMI-1640 and seven drops of human blood are added thereto. The resulting mixture is stirred well using a pipette to prepare the mixed solution with RC cells.

Figure 59:
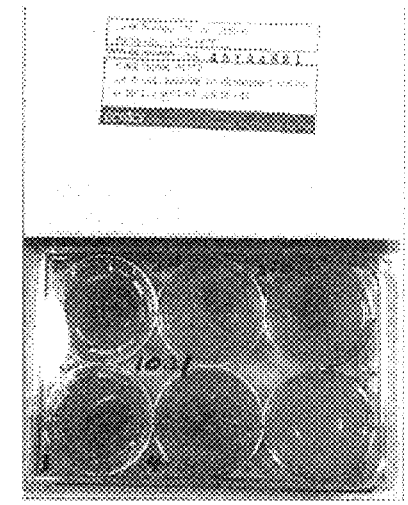
FIG. 59 is a plan view of a transwell containing sliced tissue samples.

While lifting the inner part of the transwell, three milliliters of the mixed solution are poured into the outer part of the transwell. The inner part of the transwell then is returned to the outer part, and two milliliters of RPMI-1640 are poured into the inner part. Care is taken throughout this process not to mix the solution in the inner part with that of the outer part. The tissue samples, after having been sliced into sections measuring about 5 millimeters×5 millimeters×3 millimeters, are placed into the inner part of the transwell, as shown in FIG. 59.

Next another transwell can be prepared in the same manner, but without placing the tissue sample in the inner part of the transwell. This particular transwell is provided for visual comparison with the tissue-containing ones.

In order to take a sample, the inner part is lifted out (without cleansing the bottom of the inner part) and the RC cells in the solution of the outer part are mixed well using the pipette. One drop of the solution in the outer part then is withdrawn and its initial RC quantity is measured using the Burker-Turk device. After the initial measurement, the same sample is cultured in the 37° C. 5% $CO_2$ incubator. Thereafter, the RC quantity is measured every twenty four hours. Before measuring, however, stirring is performed so that the RC cells scatter evenly in the solution.

Figures 63, 64, 65:
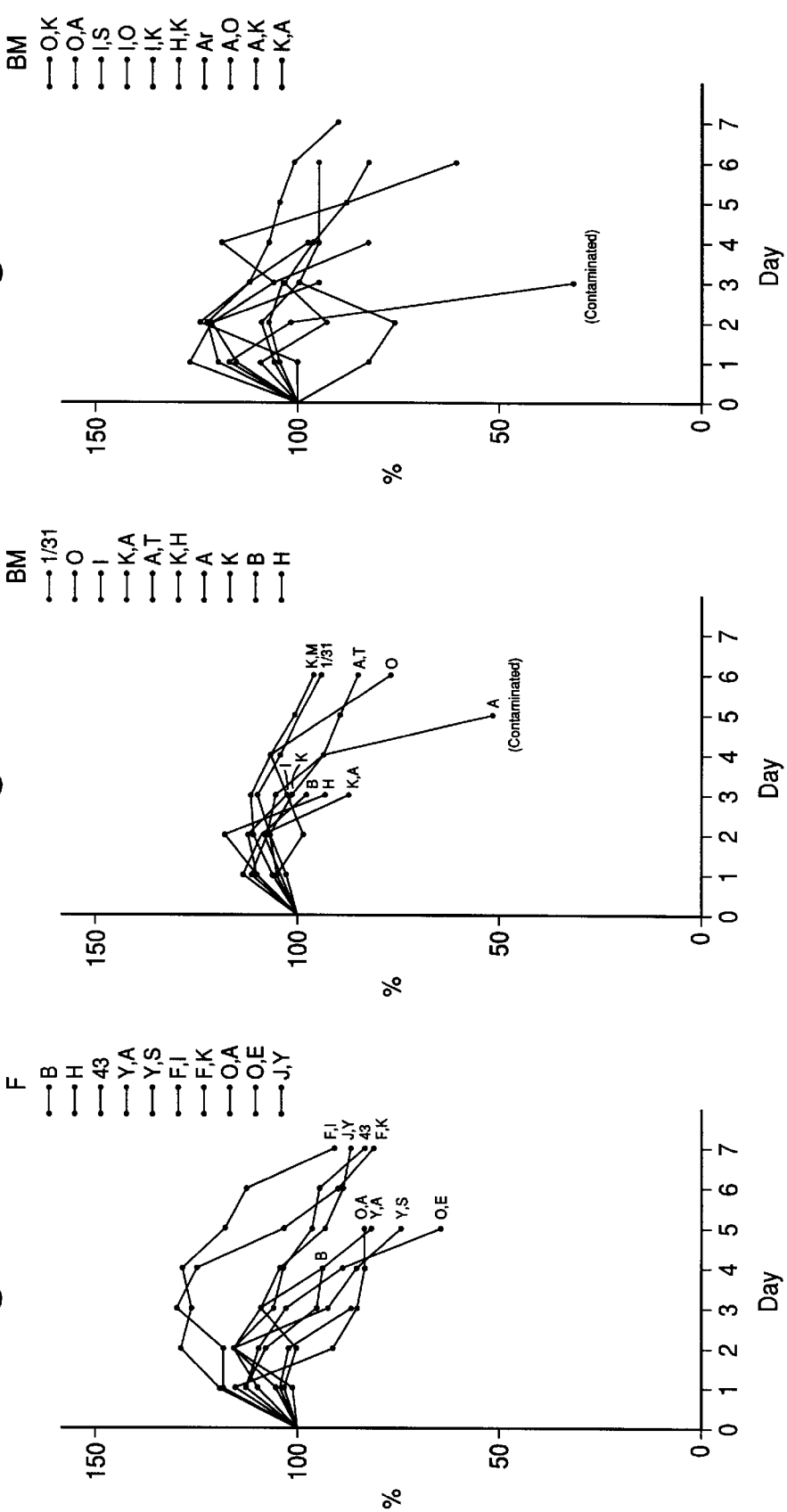

The results of the foregoing method are graphically illustrated in FIGS. 60–66. As shown in FIGS. 60 and 61, when the tissue constitutes muscle tissue, the RC increases. Likewise, as shown in FIGS. 62 and 63, when the tissue constitutes fat tissue, the RC also increases. When the tissue constitutes bone marrow, there also is an increase in RC, as shown in FIGS. 64 and 65. By contrast, when the tissue constitutes cartilage tissue, the RC decreases, as shown in FIG. 66.

The filter in each Costar transwell prevents the passage of cells and allows only watery solutions to pass through it. Regardless of this, the RC increase during culturing. This increase in RC is justified by a "cell from cell" theory. Previously, it was a universal belief that erythrogenesis is performed from the bone marrow tissue. The foregoing results, however, demonstrate that it would be premature to conclude that the process of erythropoesis is fully explained.

Notably, prior erythropoesis experiments were performed on starved animals. This apparently neglects the very fact that the cells explained by that theory can never be observed in animals which have been fed a proper diet.

Moreover, among elderly people, the bone marrow is replaced with fat, which transforms into yellow bone marrow. This, however, never causes anemia. This fact also is neglected by the traditional erythropoesis experiments.

Sportsman's anemia also remains unexplained by the traditional theory of erythropoesis from the bone marrow. Sportsman's anemia is commonly found among athletes.

When the athlete discontinues training, however, the disease is automatically cured. This cannot be explained using the traditional erythropoesis theory.

Also, observation of the bone marrow cells through culturing did not reveal the cells which are described in the hematological text books. According to the traditional erythropoesis theory, erythroblasts with cores transform themselves into erythrocyte, after losing their cores. In reality, however, not a single example is reported that the cells survive after losing their cores. The cells generally disintegrate when they lose their cores. It is questionable therefore how the erythrocytes without cores survive as an exception.

RC cannot generate erythrocyte itself since it has no DNA. The erythrocyte nevertheless increased in the method described above. This may have occurred because the RC is a very primitive cell belonging to "the RNA world."

Fish-type Red Blood Cells

Figure 68:
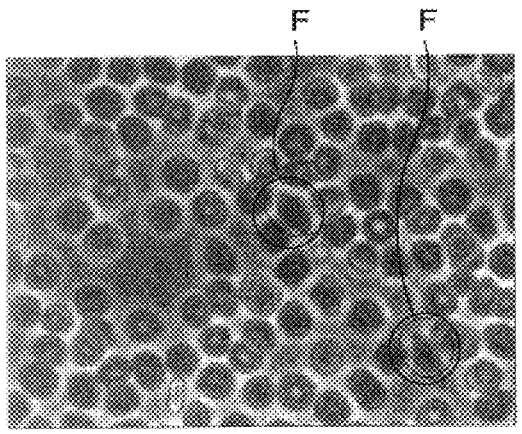
FIGS. 67 and 68 are microscopic views of lower layer (LL) RC which include RC (F) which, in turn, resemble blood cells in fish (goby).
Figure 67:
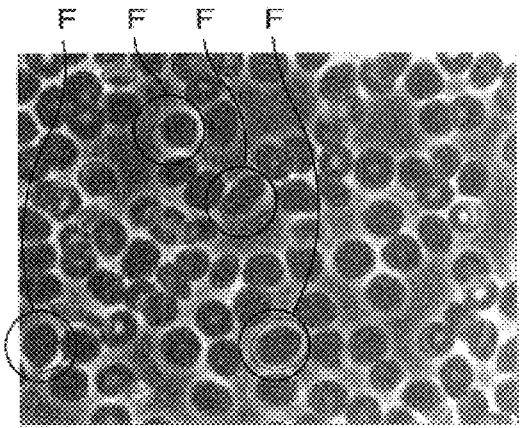
Figure 69:
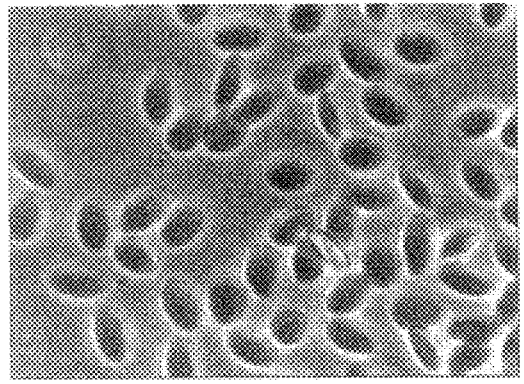
FIG. 69 is a microscopic view of cells taken from an eel.
Figure 70:
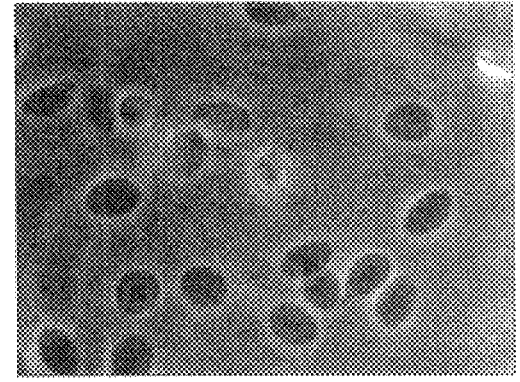
FIG. 70 is a microscopic view of goby cells.

Still another result of the method described in Example 2 is that the lower layer (LL) RC includes RC (F), as shown in FIGS. 67 and 68, that resemble blood cells in fish (goby). For purposes of comparison, FIG. 69 shows cells taken from an eel and FIG. 70 shows goby cells.

The characteristics of such cells include a thick center, a dark color, and a shape which resembles a human eye. These red blood cells can be divided roughly into two types, the eye-shaped type and the round type. These are largely observed in patients with rheumatoid arthritis, but also can be observed in a small number of healthy people. No F type RC exist in the upper layer (UL) RC or in the intermediate layer (IL) RC. It is possible therefore, based on the forgoing observations, that the F type of RC are vestiges of the fish age.

Observation of Rice-like Body

If one drop of blood taken from the cubital vein is introduced into 3 milliliters of RPMI-1640 and the resulting solution is mixed and then observed using a scanning microscope, white, shiny substances which resemble grains of rice appear in the blood, as shown in FIG. 71, when the blood is taken from a patient afflicted with articular rheumatism, anemia, or cancer. These substances are intensely active, and turn into black spots, as shown in FIG. 72. They subsequently revert to a white, shiny substance which resembles a grain of rice. This activity is repeated. Usually, after 24 hours, this activity stops suddenly, and terminates in black spots as shown in FIG. 73.

There is little possibility that this substance is a platelet. Since it is frequently observed in patients with articular rheumatism and cancer, accompanied by anemia, and iron deficiency anemia, it is presumably a substance associated with hemopoietic tissues.

Anti-coagulants

The present invention also can be applied to processes of identifying anticoagulants which do not hinder the beneficial functions of red blood cells. When a blood transfusion is performed, anti-coagulants typically are used to keep the blood from coagulating. There is very little information, however, on whether there are problems associated with such use of anti-coagulants.

A preferred method according to the present invention can be performed using any proposed anticoagulant. Examples include Heparin and sodium citrate. According to the preferred method, five milliliters of blood with the anti-coagulant and blood without the anti-coagulant are provided from the cubital vein. Both blood samples are processed as described above in Example 2.

The blood is poured into a 7% dextran saline solution and then is mixed thoroughly. The resulting solution then is left stationary for about one hour at room temperature (20 to 23° C).

During the period of about one hour, the solution separates into three visually distinct layers. The upper layer (UL) RC contains many leukocytes. This upper layer (UL) RC is withdrawn and processed using a hypotonic solution, as described above, and then is also processed using a hypertonic solution in the manner described above. The resulting mixture then is left at room temperature for about 2 to 4 hours, after which it is placed into the 37° C. 5% $CO_2$ incubator for incubation therein.

Within 2 to 3 hours of incubation, the red blood cells in the sample which was not treated with anti-coagulants undergo metamorphosis-like changes, and develop various types of extraordinary shapes. When pseudomonas sp. are added, these cells begin to move rapidly and seem to attack the pseudomonas sp.

Figure 76:
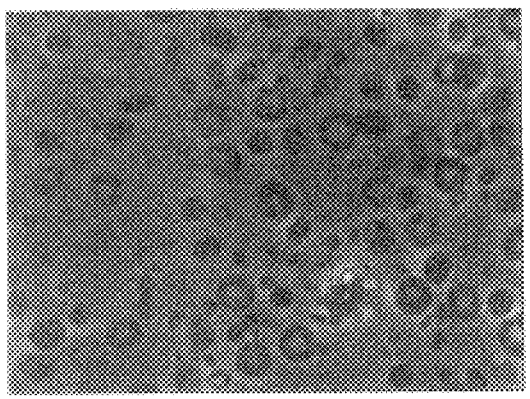
FIG. 76 is a microscopic view of the mixture illustrated in FIGS. 74 and 75 when pseudomonas sp. is added to the anti-coagulant-treated blood sample.
Figure 77:
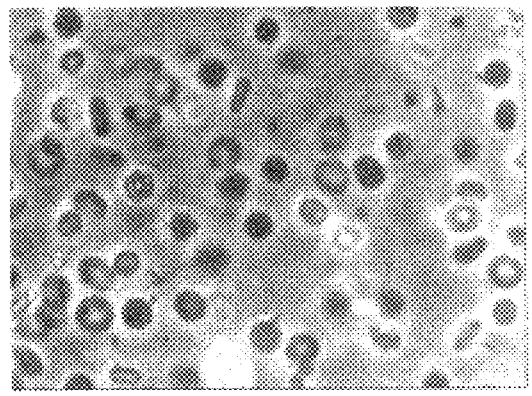
FIG. 77 is a microscopic view of the mixture shown in FIG. 76, after the cells become hard.

By contrast, in the blood with anti-coagulants (as shown in FIGS. 74 and 75), very little metamorphosis-like changes are observed. When pseudomonas sp. is added to the anti-coagulant-treated blood sample (as shown in FIG. 76), the movement decreases significantly. The cells, as shown in FIG. 77, become hard as if they were dead.

It would appear from the foregoing results that because the tested anticoagulant(s) are mostly acidic, the membranes of the red blood cells harden and do not change or go through the type of metamorphosis experienced by the other cells. As a result, they fail to exhibit the type of movement seen when anti-coagulants are not used. There is consequently no readily apparent attacking of the pseudomonas sp. by these particular cells.

In view of the important functions provided by the RC, care should be exercised when transfusing large quantities of blood (e.g., in treating pelvic fractures, multiple complicated fractures, or surgery of the spine) to avoid suppressing the RC's important functions. The present invention, by providing a way of testing proposed anti-coagulants using the above described method, advantageously facilitates identification of the types of anti-coagulants which will not suppress the important functions of red blood cells.

Red Blood Cells as a Structure for Communicating Information

The present invention also facilitates the use of red blood cells as a source for information concerning disease and abnormalities. In this regard, the present invention can be used for diagnostic purposes.

Part of what makes red blood cells so useful as a source of information is the extensiveness of the circulatory system and the speed with which blood travels throughout the body. The heart normally ejects 250 to 350 millimeters of blood in one systole. It has been reported that the ejected blood returns again to the heart in 24 to 26 seconds on average.

For adults, this means that about 21000 milliliters of blood (350 milliliters times 60 beats/minute (the typical pulse rate)) passes through the heart in one minute. In one hour, 1,260 liters of blood passes through the heart. When this volume is multiplied by 24 to determine how much blood flows through the heart in a single day, the result is 30,240 liters.

It is reasonable to assume therefore that all of the red blood cells are circulating and passing through every part of the body. Among the red blood cells which are circulating, certain types are sensitive to diseases and will be affected by such diseases. By detecting and isolating such cells, the present invention may be used to facilitate early diagnosis of certain diseases.

EXAMPLE 3

According to a third exemplary method of the present invention, one drop of blood is taken from the cubital vein and is introduced into a Costar flask. The Costar flask contains 3 milliliters of RPMI-1640. The resulting mixture is observed for a period of four weeks while it is incubated in a 37° C. $CO_2$ incubator.

Figure 78:
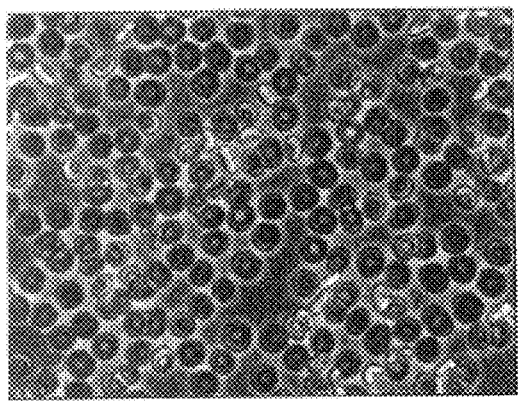
FIG. 78 is a microscopic view of a normal blood sample after having been processed according to a third example of the present invention.

FIGS. 78–81 represent four samples after an initial incubation period of 48 hours. FIG. 78 shows a normal blood sample, that is, one from a patient which remains unaffected by disease. In FIG. 78, only the known double-ring RC is visible.

Figure 79:
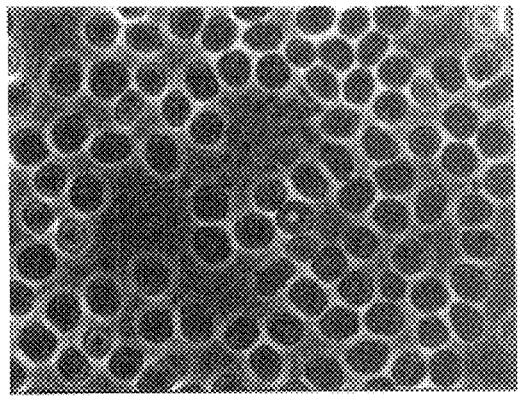
FIG. 79 is a microscopic view of a blood sample taken from a diseased patient, the sample having been processed according to the third example of the present invention.

In the sample which appears in FIG. 79, by contrast, scattered spots are visible. The sample in FIG. 79 was taken from a diseased patient.

Figure 80:
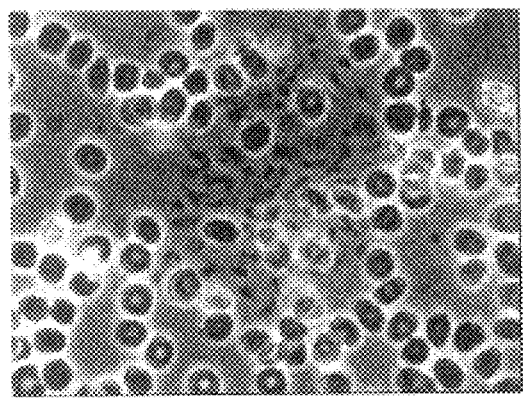
FIG. 80 is a microscopic view of a blood sample taken from another diseased patient, the sample having been processed according to the third example of the present invention.

The sample shown in FIG. 80 includes grouped spots. This sample also was taken from a diseased patient.

Figure 81:
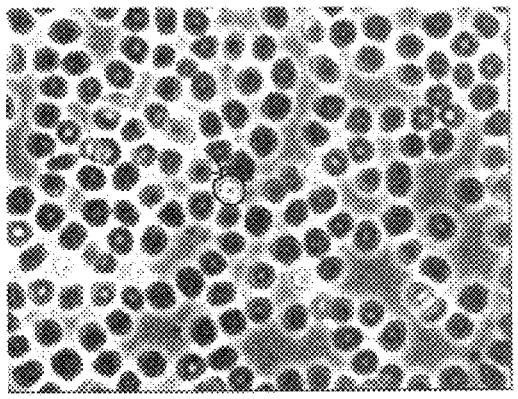
FIG. 81 is a microscopic view of a blood sample taken from a diseased patient, in which spots and deformed RC are visible.

In the sample shown in FIG. 81, spots and deformed RC are visible. The sample shown in FIG. 81 also was taken from a diseased patient.

Figure 82:
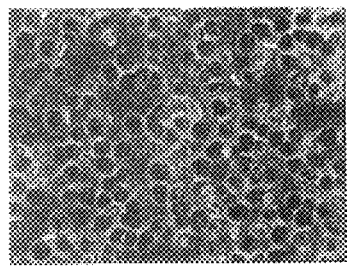
FIG. 82 is a microscopic view of a sample taken from a patient which was unaffected by disease, and after an intermediate incubation period of 5 to 14 days (±4 days).
Figure 83:
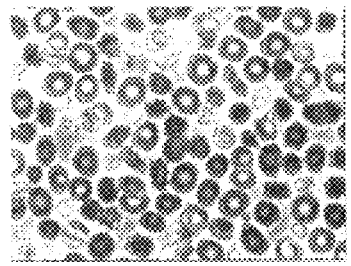
FIG. 83 is a microscopic view of a sample taken from a diseased patient, the sample having been incubated for an intermediate incubation period of 5 to 14 days (±4 days).
Figure 84:
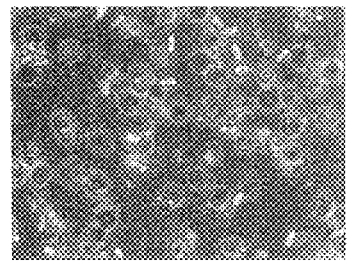
FIG. 84 is a microscopic view of a sample taken from a diseased patient, the sample having been incubated for an intermediate incubation period of 5 to 14 days (±4 days).
Figure 85:
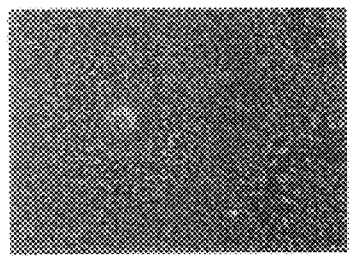
FIG. 85 is a microscopic view of a sample taken from a patient which was not affected by disease, the sample having been incubated for a terminal incubation period extending from the intermediate period to the $28^{th}$ day.

FIGS. 82–84 show three samples after an intermediate incubation period of 5 to 14 days (±4 days). The sample shown in FIG. 82 was taken from a patient which was unaffected by disease. The cells which have been slightly deformed or which have some black dust-like markings will attach at the bottom.

FIG. 83, by contrast, shows a sample taken from a diseased patient. The deformation of the RC (Bc cell, Yc cell) is remarkable, and ghost cells emerge as well.

FIG. 84 shows another sample taken from a diseased patient. In the sample shown in FIG. 84, large white shiny particles, large yellow shiny particles, and cells that are yellow in their surrounding parts and brown in their centers become readily apparent.

FIGS. 85–90 show samples after a terminal incubation period extending from the intermediate period to the 28$^{th}$ day. The sample in FIG. 85 was taken from a patient which was not affected by disease. In the sample shown in FIG. 85, black sesame-like grainy particles appear, as do cluster circles.

Figure 86:
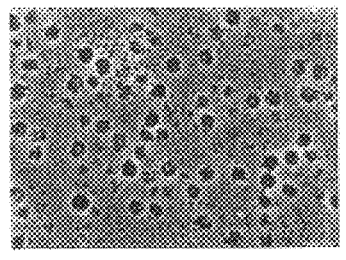
FIG. 86 is a microscopic view of a sample taken from a diseased patient, the sample having been incubated for the terminal incubation period.

FIG. 86, by contrast, shows a sample which contains pits and apoptosis. This sample was taken from a diseased patient.

Figure 87:
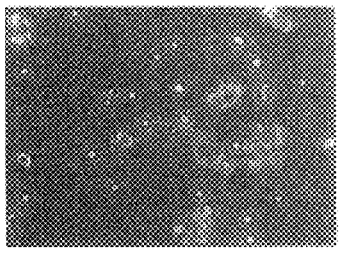
FIG. 87 is a microscopic view of a sample taken from a diseased patient, wherein particles with yellow peripheral portions and orange centers become visible.

FIG. 87 also shows a sample taken from a diseased patient. In the sample shown in FIG. 87, particles with yellow peripheral portions and orange centers become visible.

Figure 88:
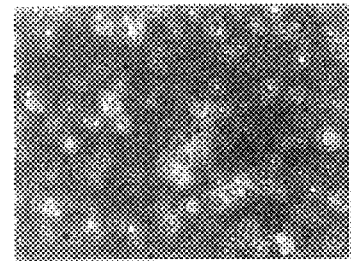
FIG. 88 is a microscopic view of a sample having shiny, white particles.

FIG. 88 shows a sample having shiny, white particles. The sample shown in FIG. 88 also was taken from a diseased patient.

Figure 89:
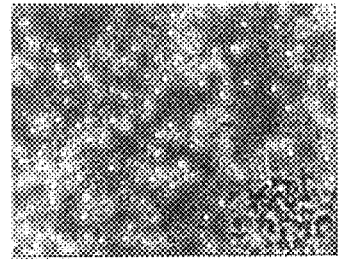
FIG. 89 is a microscopic view of a sample having shiny, yellow particles.

FIG. 89 shows a sample having shiny, yellow particles. The sample shown in FIG. 89 also was taken from a diseased patient.

Figure 90:
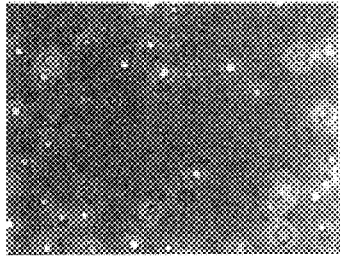
FIG. 90 is a microscopic view of a sample which contains ghost cells.

The sample shown in FIG. 90 contains ghost cells. This sample also was taken from a diseased patient.

The present invention thus facilitates the diagnoses of certain diseases.

Cancer

The present invention, for example, facilitates diagnosis of cancer.

Initially, one drop of peripheral blood is added to RPMI-1640 and the resulting mixture is incubated in a 37° C. $CO_2$ incubator. Thereafter, the incubated mixture can be observed using, for example, the method described above as example 3.

Alternatively, the methods described in examples 1 and/or 2 can be used to separate the blood into the three aforementioned visually distinguishable layers and to withdraw the various samples of the upper layer (UL) RC, intermediate layer (IL) RC, and lower layer (LL) RC. The samples then can be incubated in a 37° C. $CO_2$ incubator and observed regularly.

During the initial period of incubation (within 48 hours), the blood samples from cancer patients begin to exhibit RC with distinguishing features (i.e., RCRC). Many RC will change shape or will be transformed when the samples are from cancer patients.

During the terminal period (e.g., 16±4 days), ghost cells, bright white (B.W.) particles, bright yellow (B.Y.) particles, and brown masses appear but no cluster circles develop in the samples which are taken from cancer patients.

In the samples taken from healthy patients, by contrast, small black cerame particles are scattered and cluster circles appear among them.

When the methods described in examples 1 and 2 are implemented, the following results are achieved in samples from stomach cancer patients and lung cancer patients. Each "+" symbol denotes several occurrences of the indicated feature. The term "Sol" refers to a colloid dispersion liquid.

| Layer | 1 Hour | Initial Period (after 48 hours) | Middle Period (5–15 days) | Terminal Period (>15 days) |
| --- | --- | --- | --- | --- |
| Upper Layer RC | 1. Rice Grain +++<br>2. Altered RC ++<br>3. Sol | 1. Disappears<br>2. Altered, Transformed RC ++++<br>3. Gel ++ | 2. Altered, Transformed Cells ++++<br>3. Become Gel Again | Altered (Notched) Cell Transformed (YCC) Cell<br>3. Sol |
| Intermediate Layer RC | 1. Rice Grain ++<br>2. Altered RC ++<br>3. Sol | 1. Disappears<br>2. Altered, Transformed RC ++<br>3. Gel ++ | 2. Altered, Transformed Cells ++<br>3. Gel +++ | Become Unique Dust-Like Shape<br>3. Semi-gel |
| Lower Layer RC | 1. Normal RC<br>2. Sol | 1. Normal RC<br>2. Sol | 1. Normal RC<br>2. Sol<br>3. Ghost Appear at Times | Possible Apoptosis (Suddenly Become Black Spots) |

Figure 91:
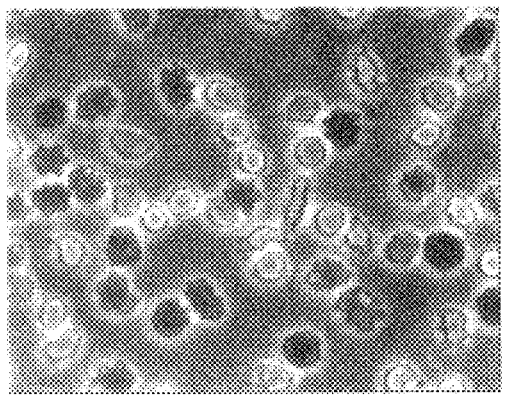
FIG. 91 is a microscopic view of a sample taken from a gastric cancer patient, the sample having been incubated for a period of 20 days.

FIG. 91 shows a sample taken from a gastric cancer patient. The sample which appears in FIG. 91 was incubated for a period of 20 days. Notably, FIG. 91 shows altered (notched) cells from the upper layer (UL) which are deformed.

Figure 92:
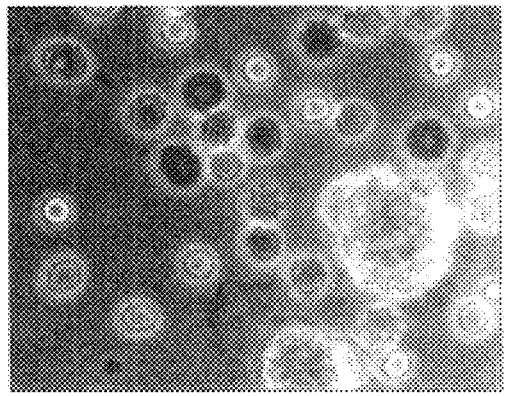
FIG. 92 is a microscopic view of altered cells after incubation for a period of 20 days in a sample of the upper layer (UL) which was taken from a lung cancer patient.

FIG. 92 shows similarly altered cells from a sample which was taken from a lung cancer patient. The sample in FIG. 92 also was taken from the upper layer (UL) and was incubated for a period of 20 days.

Figure 93:
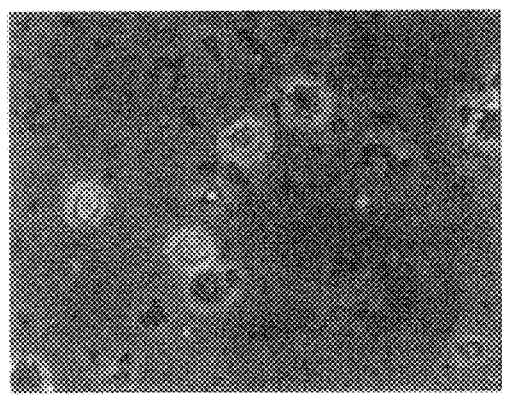
FIG. 93 is a microscopic view of an intermediate layer (IL) sample after 20 days of incubation, taken from a gastric cancer patient.
Figure 94:
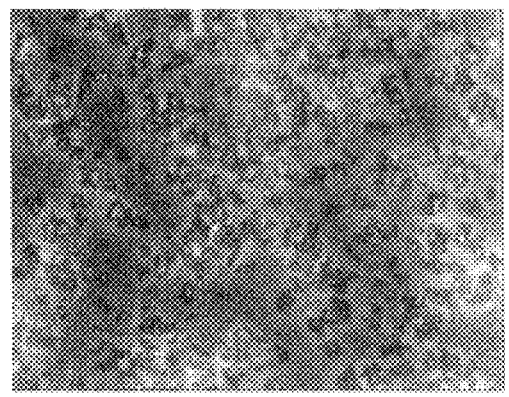
FIG. 94 is a microscopic view of an intermediate layer (IL) sample after 20 days of incubation, taken from a lung cancer patient.

FIG. 93 shows a sample taken from a gastric cancer patient. The sample which appears in FIG. 93 was incubated for a period of 20 days and was taken from the intermediate layer (IL). The sample includes a semi-gel, rarely observed intermediate layer (IL) RC, and dust and ghost cells. FIG. 94 also shows a sample after an incubation period of 20 days. The sample in FIG. 94, however, was taken from a lung cancer patient. In FIG. 94, the rarely observed intermediate layer (IL) RC and dust are also visible.

Figure 95:
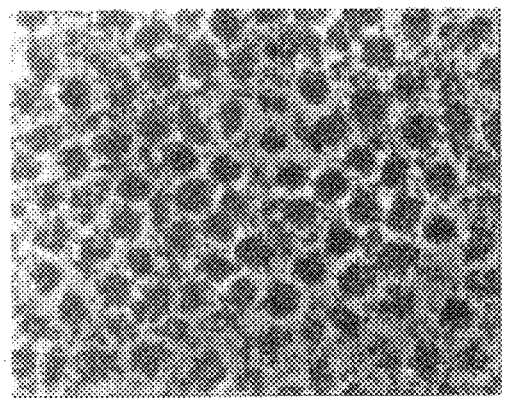
FIGS. 95 and 96 are microscopic views of samples after an incubation period of 20 days, taken from the lower layer (LL), with the sample of FIG. 95 having been taken from a gastric cancer patient and the sample of FIG. 96 having been taken from a lung cancer patient.
Figure 96:
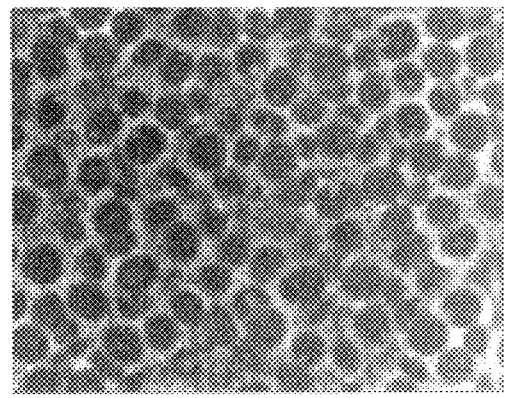

FIGS. 95 and 96 show samples after an incubation period of 20 days. Both samples were taken from the lower layer (LL), with the sample of FIG. 95 having been taken from a gastric cancer patient and the sample of FIG. 96 having been taken from a lung cancer patient. FIGS. 95 and 96 both show what appears to be apotosis. FIG. 95 includes pockmark-like spots.

The same methodology was applied to samples which were taken from colon cancer patients and separated into the three visually distinct layers, namely, the upper layer (UL), intermediate layer (IL), and lower layer (LL). The observations were substantially the same.

For purposes of comparison, the following chart describes the results for samples taken from healthy patients. In the chart, each "+" symbol denotes several occurrences of the indicated feature. The symbol "±" indicates that few occurrences of the feature can be found in the sample, but it may require searching through the sample. The symbol "−" indicates that the feature cannot be found in the field of vision. The term "Sol" refers to a colloid dispersion liquid.

| Layer | 1 Hour | Initial Period (after 48 hours) | Middle Period (5–15 days) | Terminal Period (>15 days) | |
|---|---|---|---|---|---|
| Upper Layer RC | 1. Rice Grain<br>2. Sol | 1. Altered, Transformed ±<br>2. Sol − | 1. Altered RC ++,<br>Transformed ++<br>2. Sol − | Black sesame, dust<br>Black sesame, dust | |
| Intermediate Layer RC | 1. Rice Grain −<br>2. Sol − | 1. Altered, Transformed ±<br>2. Sol − | 1. Altered RC ++<br>Transformed ++<br>2. Sol − | Black sesame, dust<br>Black sesame, dust | |
| Lower Layer RC | 2. Sol − | 2. Sol − | 2. Sol − | Black sesame, dust<br>Black sesame, dust | |

After comparing the foregoing results, it becomes apparent that the upper layer (UL) RC and the intermediate layer (IL) RC in samples which are taken from cancer patients react very differently from those which are taken from healthy patients. In an incubation solution that has turned to gel (or has become quite viscous), the growth of pseudomonas sp. is extremely suppressed, whereas the surviving time of the RC becomes very long.

When the lower layer (LL) RC are compared using samples taken from cancer patients and those of healthy patients, both exhibit substantially the same characteristics.

Instead of using the methods described in examples 1 and/or 2, it is possible to apply the methods of example 3 to samples taken from liver cancer and breast cancer patients. Initially, one drop of peripheral blood is added to RPMI-1640 and the resulting mixture is incubated in a 37° C. $CO_2$ incubator. Thereafter, the incubated mixture is observed using the method described above as example 3.

FIG. 97 shows the sample taken from the liver cancer patient after 24–48 hours of incubation. FIG. 98 shows the sample taken from the breast cancer patient after 24–48 hours of incubation.

Rheumatoid Arthritis

The present invention also can be used in connection with the treatment and/or diagnosis of rheumatoid arthritis. As shown in FIGS. 99 and 100, a sample taken from a rheumatoid arthritis patient after the initial incubation period includes many scattered RC (shown in FIG. 99), as well as many spots and groupings (as shown in FIG. 100).

During the intermediate incubation period, many blue charcoal cells (BCC) and altered cells, as well as many ghost cells, can be observed in the sample taken from a rheumatoid arthritis patient. The quick ones disappear in about 1 week, developing into dust.

During the terminal incubation period, there are masses of big yellow dust and rather small white dust in the sample taken from the rheumatoid arthritis patient. The number of those that do not form cluster circles are overwhelmingly large, though there may be a small number of those that do form incomplete cluster circles, as shown in FIG. 101. These yellow dust and smaller white dust look very similar to those seen at the time of virus infection (herpes virus infection). However, when these cases are ameliorated by incubated white blood cell infusion therapy, the alterations becomes mild, and become similar to those of normal people. It, however, does not become identical to those of healthy people.

Figure 102:
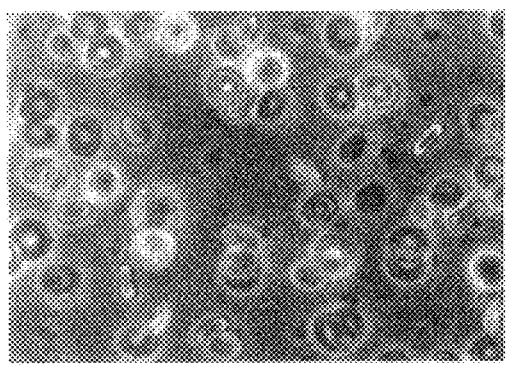
FIGS. 102, 103 and 104 are microscopic views of the upper layer (UL), intermediate layer (IL), and lower layer (LL), respectively, of a sample taken from a rheumatoid arthritis (stage 1, class 2) patient, at the beginning of incubation.
Figure 103:
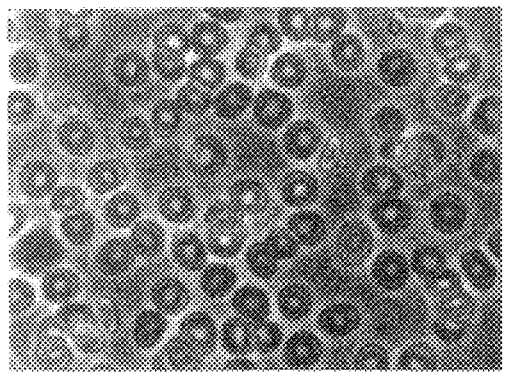
Figure 104:
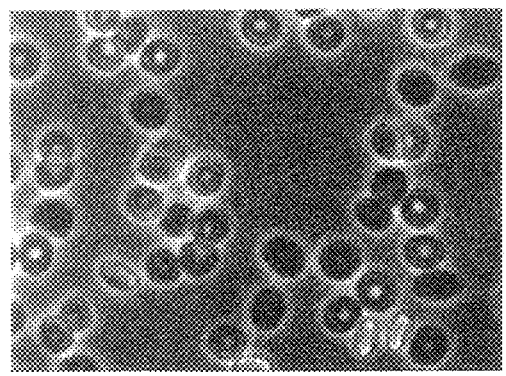

FIGS. 102, 103 and 104 show the upper layer (UL), intermediate layer (IL), and lower layer (LL), respectively, of a sample taken from a rheumatoid arthritis (stage 1, class 2) patient, at the beginning of incubation. In FIG. 102, many bright and dark rice bodies can be observed, and relatively many leukocytes in the upper layer (UL). In FIG. 103, few bright and dark rice bodies can be observed, and the RC are almost normal. In FIG. 104, fish type RC and normal RC can be observed.

Figure 105:
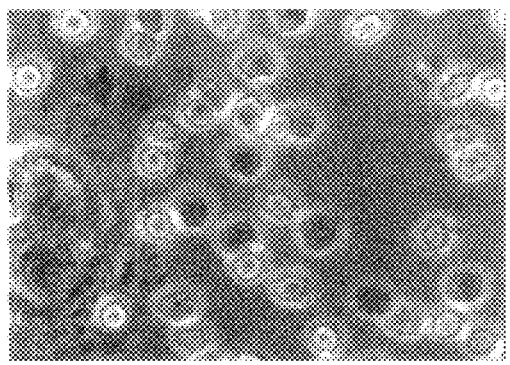
FIGS. 105, 106 and 107 are microscopic views of the upper layer (UL), intermediate layer (IL), and lower layer (LL), respectively, of a sample taken from a rheumatoid arthritis (stage 1, class 2) patient, after having been incubated for 12 days.
Figure 106:
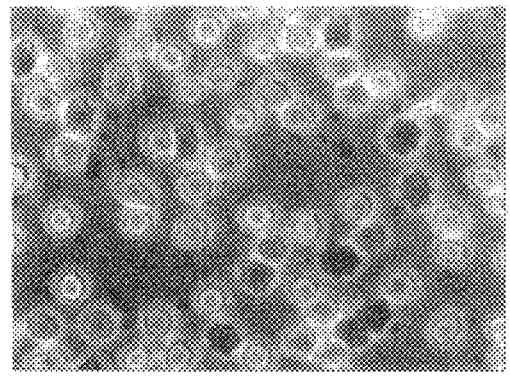
Figure 107:
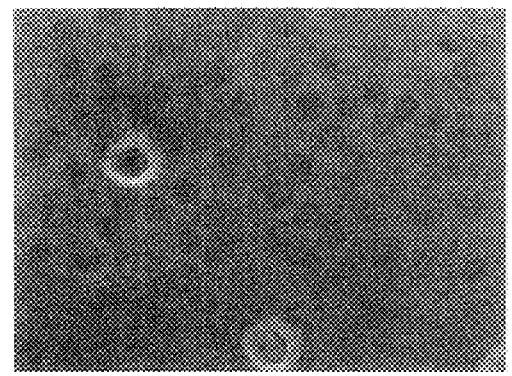

FIGS. 105, 106 and 107 show the upper layer (UL), intermediate layer (IL), and lower layer (LL), respectively, of a sample taken from a rheumatoid arthritis (stage 1, class 2) patient. The samples in FIGS. 105, 106, and 107 had been incubated for 12 days. In FIG. 105, a large leukocyte and various changed RC are visible. In FIG. 106, many dark spots and various changed RC can be observed. In FIG. 106, many ghost cells and very few living RC can be observed.

Crohn's Disease and Colitis Ulcerative.

Figure 108:
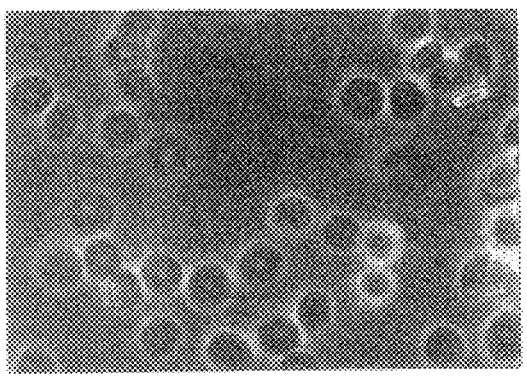
FIGS. 108, 109 and 110 are microscopic views of the upper layer (UL), intermediate layer (IL), and lower layer (LL), respectively, of a sample taken from a colitis ulcerative patient, after having been incubated for 3.5 hours.
Figure 109:
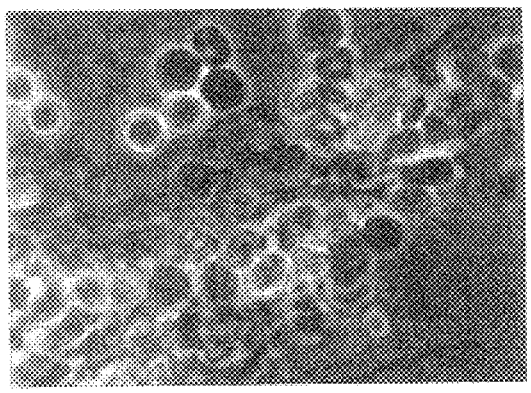
Figure 110:
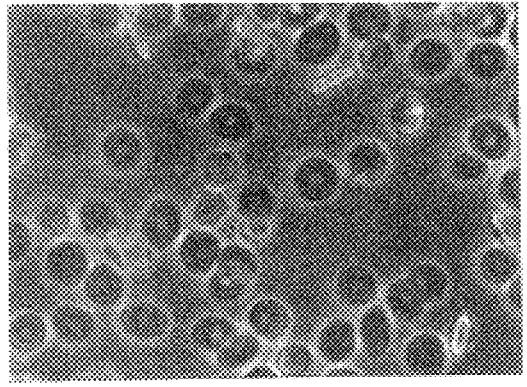

FIGS. 108, 109 and 110 show the upper layer (UL), intermediate layer (IL), and lower layer (LL), respectively, of a sample taken from a colitis ulcerative patient. The samples in FIGS. 108, 109, and 110 had been incubated for 3.5 hours. In FIG. 108, there are slightly changed RC and a hair-like feature in the sample. In FIG. 109, many dirty dark spots appear, as do a lot of hair-like features and various RC. In FIG. 110, there are slightly changed RC and normal RC.

Figure 111:
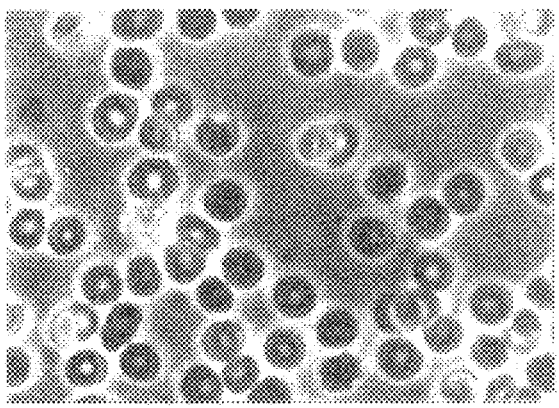
FIGS. 111, 112 and 113 are microscopic views of the upper layer (UL), intermediate layer (IL), and lower layer (LL), respectively, of a sample taken from a colitis ulcerative patient, after having been incubated for 4 hours.
Figure 112:
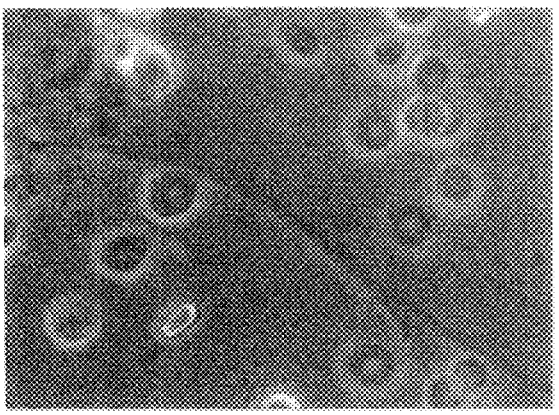
Figure 113:
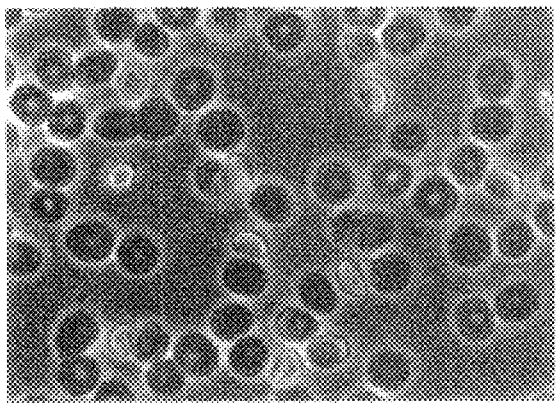

FIGS. 111, 112 and 113 show the upper layer (UL), intermediate layer (IL), and lower layer (LL), respectively, of a sample taken from a colitis ulcerative patient. The samples in FIGS. 111, 112, and 113 had been incubated for 4 hours. In FIG. 111, there are slightly deformed RC in the sample. In FIG. 112, many dirty spots appear, as does a large hair-like feature. In FIG. 113, there are slightly changed RC.

Figure 114:
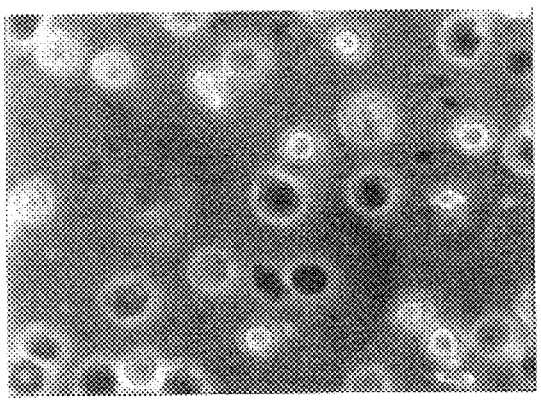
FIGS. 114, 115 and 116 are microscopic views of the upper layer (UL), intermediate layer (IL), and lower layer (LL), respectively, of a sample taken from a colitis ulcerative patient.
Figure 115:
Figure 116:
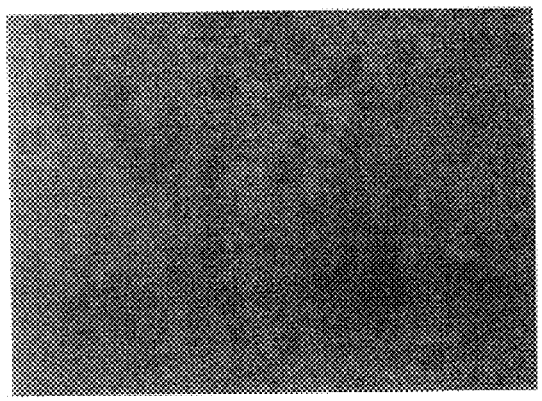

FIGS. 114, 115 and 116 show the upper layer (UL), intermediate layer (IL), and lower layer (LL), respectively, of a sample taken from a colitis ulcerative patient. The samples in FIGS. 114, 115, and 116, however, had been incubated for a period of 16 days. In FIG. 114, there are deformed RC caused perhaps by steroid H. In FIG. 115, many dirty spots changed and the hair-like feature is larger than that of FIG. 109. In FIG. 116, ghost cells can be observed in the sample.

For purposes of comparison, FIGS. 117–125 show samples similar to that of FIGS. 108–116, but taken from an Crohn's disease patient.

Figure 117:
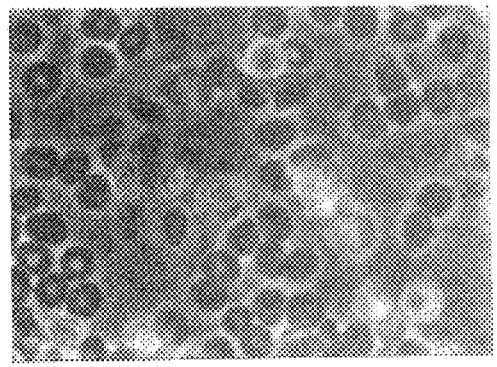
FIGS. 117, 118 and 119 are microscopic views of the upper layer (UL), intermediate layer (IL), and lower layer (LL), respectively, of a sample taken from a Crohn's disease patient, after having been incubated for 3.5 hours.
Figure 118:
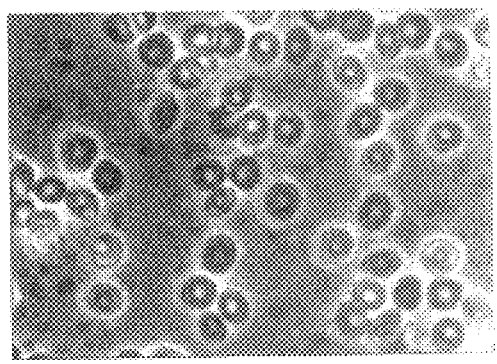
Figure 119:
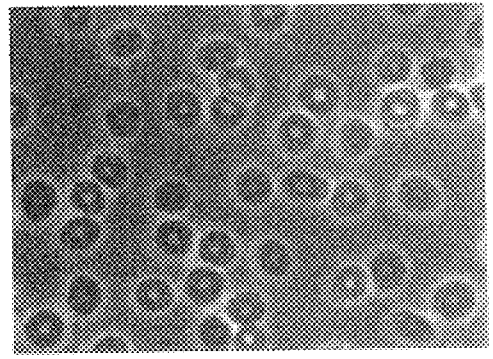

FIGS. 117, 118 and 119, for example, show the upper layer (UL), intermediate layer (IL), and lower layer (LL), respectively, of a sample taken from a Crohn's disease patient. The samples in FIGS. 117, 118 and 119 had been incubated for 3.5 hours. In FIG. 117, many dirty dark spots and various changed RC appear. In FIG. 118, many small dark spots and almost normal RC can be observed. In FIG. 119, a few dark spots and almost normal RC can be observed.

FIGS. 120, 121 and 122 show the upper layer (UL), intermediate layer (IL), and lower layer (LL), respectively, of a sample taken from a Crohn's disease patient. The samples in FIGS. 120, 121 and 122 had been incubated for 4 hours. In FIG. 120, many dirty spots and big hair-like features appear. In FIG. 121, many dirty spots and slightly deformed RC are visible. This resembles samples from rheumatoid arthritis patients. In FIG. 122, RC which are almost normal can be observed.

FIGS. 123, 124 and 125 show the upper layer (UL), intermediate layer (IL), and lower layer (LL), respectively, of a sample taken from a Crohn's disease patient. The samples in FIGS. 123, 124 and 125, however, had been incubated for a period of 16 days. In FIG. 123, there are changed RC and many dirty spots. In FIG. 124, there are changed RC and many spots. This also resembles samples taken from rheumatoid arthritis patients. In FIG. 125, apotosis may have occurred. Dark dishes are visible in FIG. 125.

Conclusion

From the foregoing and other implementations of the present invention, the following conclusions can be drawn from the observed changes (e.g., the appearance of various shapes of spots, the deformation of RC (including normal RC and derived RC) and the spots):

1. The case of colitis ulcerative:
   In the samples of the upper layer (UL) RC and intermediate layer (IL) RC taken from the blood of an ulcerative colitis patient, the degree of observed changes was smaller than those from patients of colon cancer and Crohn's disease.
2. The case of Crohn's disease:
   In the samples of the upper layer (UL) RC and intermediate layer (IL) RC taken from blood of a Crohn's disease patient, the observed changes were similar to those seen in the samples taken from the blood of a patient suffering from a severe stage of rheumatoid arthritis.
3. The case of colon cancer:
   In the samples of the upper layer (UL) RC and intermediate layer (IL) RC taken from blood of a colon cancer patient, the same changes were observed as with the samples taken from patients suffering from other types of cancer.

Chemotherapy

Figure 126:
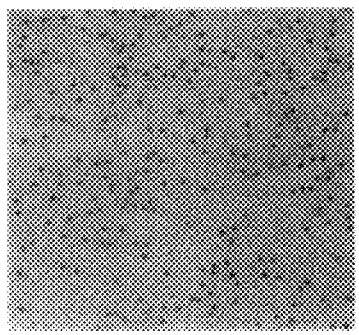
FIG. 126 is a microscopic view of the type customarily used when counting red blood cells for purposes of determining chemotherapy administration.

The present invention also has significant uses in connection with chemotherapy. When chemotherapy is administered, the traditional way to check for the existence of anemia was to count the number of red blood cells in the peripheral blood of the patient. Because the magnification used during such testing typically is only 100, as shown in FIG. 126, no attention has been directed to changes in the red blood cells themselves. Instead, attention has been directed only to the number of cells.

Figure 127:
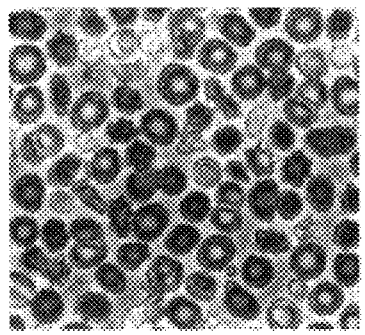
FIG. 127 is a microscopic view of a solution made, according the method of example 3, by mixing and incubating a drop of peripheral blood taken during administration of anti-cancer drugs, with 3 milliliters of RPMI-1640.
Figure 128:
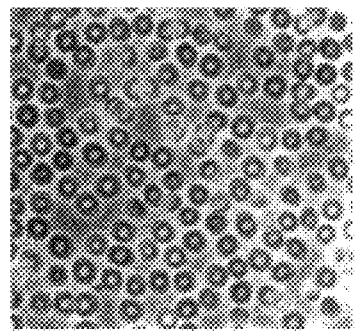
FIG. 128 is a microscopic view of altered or transformed red blood cells.

The present invention, however, provides an alternative to the traditional technique. By using the methods described as examples 1–3 during administration of anti-cancer drugs, major alterations and transformations of the red blood cells can be readily observed. In applying the method of example 3, for example, a drop of peripheral blood is added to 3 milliliters of RPMI-1640 and the resulting solution is incubated in a 37° C. $CO_2$ incubator, as shown in FIG. 127. The altered or transformed red blood cells, as shown in FIG. 128, probably are no longer normal red blood cells in that they can no longer perform their functions fully. Despite their limited capacity in this condition, large numbers of such cells would preclude a determination that the patient is anemic using the traditional technique of merely counting the cells. As a result, additional anti-cancer drugs might be administered.

Using the methods provided by the present invention, the quality of the red blood cells can be examined before anti-cancer drugs are administered. Moreover, because the red blood cells that alter or transform themselves exist in overwhelmingly large numbers in the upper layer (UL) RC and intermediate layer (IL) RC, which govern the natural healing ability, the present invention can be used to determine how anti-cancer drugs (chemotherapy) can be administered in such a way as to avoid destruction of the upper layer (UL) RC and intermediate layer (IL) RC.

Generally, patients that receive chemotherapy become anemic. If a blood sample from such a patient is observed using a scanning microscope, various deformed erythrocytes become visible. The present invention can be applied to the research of such deformed erythrocytes.

Figure 129:
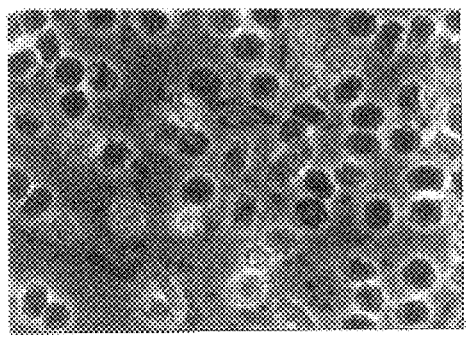
FIG. 129 is a microscopic view of deformed RC cells.
Figure 130:
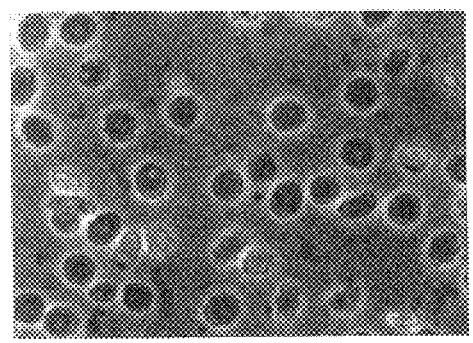
FIG. 130 is a microscopic view of a mixture of deformed RC cells with those which are normal and some roundis precipitates.
Figure 131:
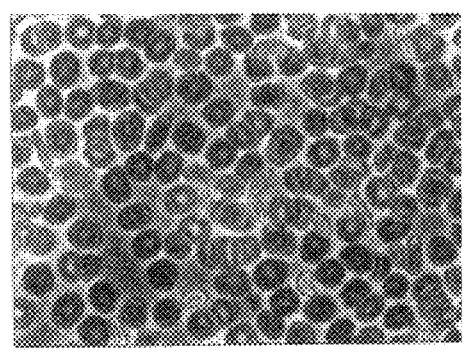
FIG. 131 is a microscopic view of some normal RC cells and precipitates.
Figure 142:
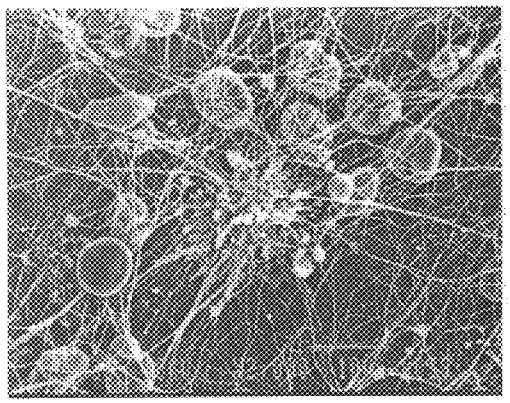
Figure 143:
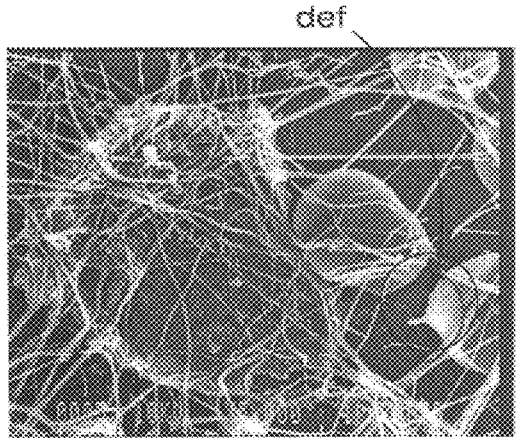
Figure 144:
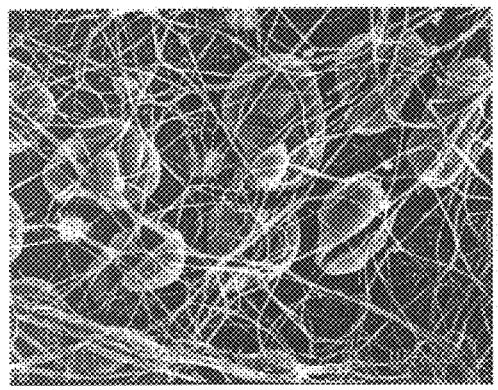
Figure 145:
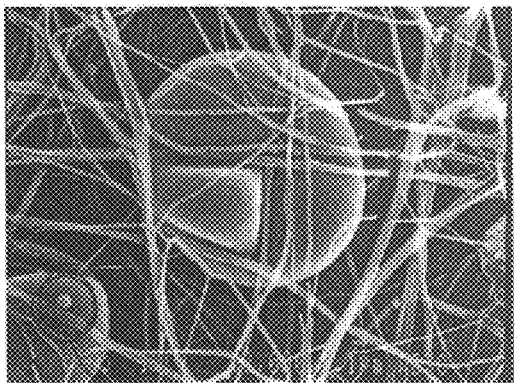
Figure 146:
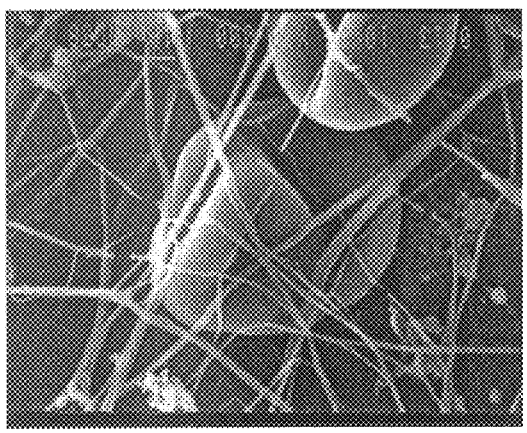
Figure 147:
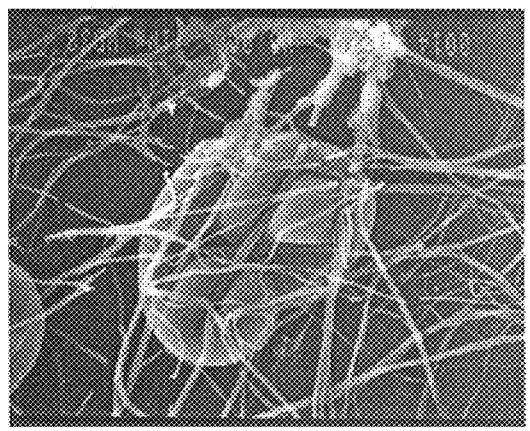
Figure 148:
Figure 149:
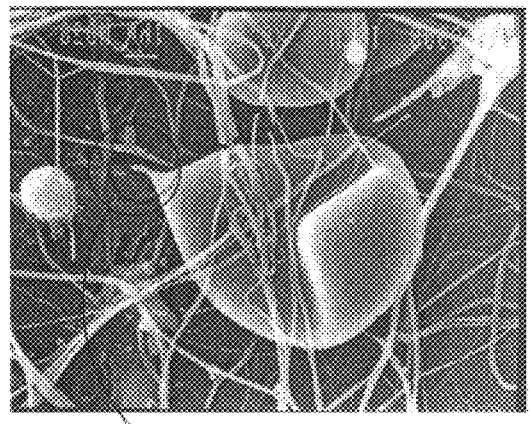

According to a preferred method, the procedures set forth in example 1 and/or example 2 are used. In particular, a five milliliter blood sample from a chemotherapy patient is mixed with 7.5 milliliters of 7% Dextran saline solution. The resulting mixture then is stirred and subsequently left for one hour at room temperature. During the one hour period, the solution becomes separated into the three visually distinguishable layers described above, namely, the upper layer (UL) RC, intermediate layer (IL) RC, and the lower layer (LL) RC. The following table indicates what is observed when each layer is viewed using a scanning microscope, and how the observed features compare with that of a healthy patient:

| Layer | Cancer Patients | Healthy Person |
| --- | --- | --- |
| Upper | Deformed RC cells, as shown in FIG. 129 and abundant filthy precipitates ++ | Normal RC cells only |
| Intermediate | Mixture of deformed RC cells with those which are normal. Some roundis precipitates ++, as shown in FIG. 130 | Normal RC cells only |
| Bottom | Normal RC cells and precipitates +, as shown in FIG. 131 | Normal RC cells only |

Since the RC in the upper layer (UL) and in the intermediate layer (IL) contain some significant functions, probably connected with natural healing, the RC should be examined using at least one of the methods provided by the present invention (e.g., examples 1 and 2) prior to administering chemotherapy to a patient and/or during the development of chemotherapy drugs and regimens.

Benefits

The various functions provided by the different types of red blood cells therefore works effectively for purposes of medical examination, diagnosis, and treatment of various diseases. The upper layer (UL) RC and the intermediate layer (IL) RC are especially effective. As indicated above, the upper layer (UL) RC obtained using the present invention are:

1. effective as a medicine to strengthen natural healing power. (This is contrary to the traditional techniques in medicine of acting directly on the diseased structure or organization only. Instead, the upper layer (UL) RC and the intermediate layer (IL) RC obtained according to the present invention stimulate and enhance the natural healing power);
2. able to attack bacteria (According to the present invention, it is the red blood cells, not the white blood cells, that attack the bacteria);
3. effective when used for purposes of early-stage diagnosis of diseases;
4. useful for purposes of judging whether treatments for diseases are effective;
5. useful for purposes of certifying the harmfulness of antibiotics or anti-coagulants;
6. useful for purposes of certifying the harmfulness of chemotherapy, especially since chemotherapy does damage to upper layer (UL) RC.

Additional Samples

FIGS. 132–141 show additional samples which were processed according to examples 1 and 2.

The sample illustrated in FIG. 132 is one which was taken from a patient which had been given chemotherapy. The samples shown in FIGS. 133, 134 and 135 are the upper layer (UL), intermediate layer (IL), and lower layer (LL), respectively, from a patient afflicted with rheumatoid arthritis.

The samples shown in FIGS. 136, 137 and 138 are the upper layer (UL), intermediate layer (IL), and lower layer (LL), respectively, from a patient afflicted with colon cancer.

FIGS. 139, 140 and 141 show the upper layer (UL), intermediate layer (IL), and lower layer (LL), respectively, of a sample which was infected with bacteria and which was treated with an antibiotic, the sample having been incubated for 28 to 29 hours in the case of the UL and IL and 24 hours in the case of the LL. In FIG. 139, there was no multiplication of the bacteria. In FIG. 140, it appears that a minute amount of bacterial multiplication occurred. FIG. 141, by contrast, shows an overwhelming amount of bacterial multiplication.

FIGS. 142–149 are electron micrograms of the upper layer (UL) RC from a rheumatoid arthritis patient. Deformations (def) of the upper layer (UL) RC can be observed in FIGS. 142–149.

When electron microscope analysis is applied to each of the three visually distinguishable layers, which are fractionated according to the present invention, their microstructures are readily observable and their activities in suppressing the proliferation of bacteria also can be observed.

The following chart indicates the microstructure observations for each of the three visually distinct layers:

| Layer | Healthy Person | Patient |
| --- | --- | --- |
| Upper & Intermediate | A red blood cell has a smooth surface and a flat circular shape, on which there are few projections and bur-like structures | A red blood cell has many projections and bur-like structures around itself which extend from the surface thereof. It is found that an electron density in the bur-like structures is high |
| Lower | Normal | Normal |

The upper layer (UL), intermediate layer (IL), and lower layer (LL) which were taken from a healthy person and mixed with cultivated pseudomonas sp. acted differently on the bacteria. Projections and bur-like structures appear on the surface of the red blood cell in the upper layer (UL) and intermediate layer (IL). Especially in the upper layer (UL), the bur-like structure adheres to and cuts into the cell wall of the pseudomonas sp.

In the lower layer, by contrast, no bur-like structure is found. Numerous pseudomonas sp. proliferate around the red blood cells.

It therefore can be concluded that the upper layer (UL) RC and the intermediate layer (IL) RC include factors which suppress the proliferation of bacteria. In view of the microstructural observations, projections and bur-like structures are strongly related to the factors.

Addition Research

The present invention also can be used for additional research on bacteria, developing methods that would enhance the natural healing power, finding alternative ways to separate and incubate red blood cells, researching the host-bacterial balance, identifying enzymes that exist in tissues and which dissolve bacteria, conducting research on cancer, and conducting research on AIDS.

With regard to the additional research on bacteria, the present invention can be applied to the extraction, analyzing, and synthesis of effective ingredients in RC, WC, upper layer RC, and intermediate layer RC. Upper layer RC, intermediate layer RC and WC can be incubated in large quantities, and using centrifugal separation, the upper layer can be separated and analyzed to identify the ingredients of the solution. In addition, large quantities of upper layer RC and WC solution and large quantities of intermediate layer RC and WC solution can be made. Each solution can be incubated and the ingredients after incubation can be identified and analyzed. Bacteria can be added to all of the foregoing solutions, followed by incubation to re-confirm the inhibiting action against bacterial proliferation. Substances which inhibit the proliferation of the bacteria then can be synthesized and added using other process steps to the ingredients to develop strongly effective medicine.

The present invention also can be used to further develop the natural healing powers. In this regard, the upper layer (UL) RC, intermediate layer (IL) RC, the WC, and the like, can be placed in the outer part of Costar's transwell, and tissues and various medicines can be placed in the inner part of the transwell, with the combination being incubated to determine more about the substances that promote the proliferation of the upper layer (UL) RC, intermediate layer (IL) RC, and the WC, as well as ways to administer it. In addition, the upper layer (UL) RC, intermediate layer (IL) RC, and the WC can be incubated using the same method to develop substances that improve the function (promote secretion) of these cells and ways to administer it.

The present invention also can be used to develop additional versions of examples 1 and 2 which provide separation and incubation of red blood cells, and which facilitate research on the function of each cell, for example, in connection with the aforementioned research on bacteria and developing methods to enhance the natural healing powers. Examples of the new version can include solar methods, articular liquid methods, alcohol methods, NaOH methods, electrophoresis methods, magnetic phoresis methods, and centrifugal methods using enzyme to destroy cells for separation according to specific gravity.

The present invention also can be applied to the development of methods to gain knowledge about the host-bacterial balance. In this regard, the upper layer (UL) RC and intermediate layer (IL) RC of the blood from patients with various diseases can be placed in a hypotonic solution and a hypertonic solution, and the RC and RC-derived cells obtained thereby can be incubated. A certain bacterium may be added to the incubating solution to determine the degree of proliferation of the bacterium, as well as the immunological power of the patient's blood (or the body) against the bacterium, namely, the host bacterial balance between the body and the correct use of antibiotics. Such methods also can be used to discover ingredients in the patient's blood serum that are associated with unknown bacteria (a method for learning the degrees of balance between human beings and the bacteria).

The present invention also can be used for purposes of discovering enzymes that exist in the tissues and dissolved bacteria, for example, tissues that exist in the muscles, liver, brain, kidney, digestive organs, and the like, that dissolve bacteria, to provide clinical applications of such enzymes.

The present invention also can be applied to research in connection with cancer. For example, ingredients which are effective against tumors, in RC, EC, upper layer (UL) RC, and M-RC can be extracted, analyzed, synthesized using Costar's transwell. The upper layer (UL) RC, intermediate layer (IL) RC, and WC can be incubated according to the present invention in large quantities and added to tumor cells and lymph node cells and observed sequentially. Cells which attack and suppress tumor cells therefore can be identified. Such cells can be separated and incubated, and the effective ingredients can be extracted, analyzed, and synthesized. In addition, the ingredients obtained by incubation can be added to the incubating solution of the tumor cell and incubated to confirm the ingredient's effectiveness.

The present invention also can be used to develop ways to improve the natural healing powder by taking out the effective cells and placing such effective cells in the outer part of Costar's transwell. Tissues which are to serve as nutrition are placed in the inner part. Medicines then can be added to the inner part to determine which substances cause the effective cells to proliferate in the outer part.

The present invention also can be used in connection with AIDS research, as well as other research on immunologic diseases. In particular, effective ingredients against AIDS, immunologic diseases, hepatitis and the like in RC, WC, upper layer (RC), and intermediate layer (IL) RC can be extracted, analyzed, and synthesized in Costar's transwell. Large quantities of the upper layer (UL) RC, intermediate layer (IL) RC, and WC can be incubated using the methods of examples 1 and/or 2. Cells from patients of such diseases (e.g., AIDS, immunologic diseases, hepatitis, and the like) then can be added to the incubated solution and the incubation can be observed sequentially. In this manner, cells which attack and suppress the disease-related cells can be identified. Such cells then can be separated and incubated, and the effective ingredients can be extracted, analyzed, and synthesized. The effects of the ingredients which are believed to be effective then can be confirmed by adding such ingredients to incubating solutions of the disease-related cells.

Another aspect of the present invention which can be applied to research on AIDS, immunologic diseases, and the like, are the aspects of the present invention which improve the natural healing power. Effective cells obtained by the aforementioned processes can be placed into the outer part of Costar's transwell. Tissues which serve as nutrition are placed into the inner part of the transwell. Various medicines then can be placed into the inner part to identify which substances proliferate the effective cells in the outer part.

As is clear from the above description, the methods provided by the present invention can easily fractionate three different blood fractions which include red blood cells as a main component but having different functions. These three different fractions may be applied to several clinical tests such as antibacterial test and the like.

Through studies using cells of patients having AIDS, cancer, hepatitis, and the like, instead of the bacteria, as was described herein, there is great potential for the development of new, excellent therapies for those diseases.

While the preferred implementations of the present invention has been described by reference to their use in connection with red blood cells, it is understood that the present invention likewise can be applied to other types of cells, including but not limited to, while blood cells, a spermatid, an ovum, pollen, a pistil, and the like. According to the present invention, it is possible to contribute to a biotechnology such as creation of new creatures and revival of ancient creatures by defining the conditions for steps in the invention, a hypotonic solution, a hypertonic solution, a cultivation, and the like.

As many apparently widely different embodiments of this invention may be made without departing from the spirit and scope thereof, it is to be understood that the invention is not limited to the specific embodiments thereof except as defined in the appended claims.

What is claimed is:

1. Method for fractionating red blood cells of human blood into three fractions comprising following steps:
   (a) mixing human blood sample with dextran aqueous solution and maintaining said mixture stationarily for 60 to 75 min so as to fractionate this blood sample into three layers, the upper, intermediate, and lower layers;
   (b) separating said three layers into three individual samples; and
   (c) treating the upper layer sample with hypotonic solution and then adding hypertonic solution into said upper layer sample.

2. The method of claim 1, including the step of providing a saponin solution as the hypotonic solution.

3. The method of claim 1, including the step of treating the upper layer with the hypotonic solution for substantially 30 seconds.

4. The method of claim 1, including the step of treating the upper layer with the hypotonic solution for a period sufficient to create an antibacterial sample.

5. The method of claim 4, including the step of treating the upper layer with the hypotonic solution for a period sufficient to preclude excessive hemolysis.

6. The method of claim 1, including the step of centrifuging the upper layer prior to treating the upper layer with the hypotonic solution.

7. The method of claim 6, including the steps of centrifuging the upper layer for a period sufficient to precipitate red blood cells and a clear layer, and discarding the clear layer.

8. Method for producing a fraction including antibacterial red blood cells, which comprises following steps:
   (a) mixing human blood sample with dextran aqueous solution and maintaining said mixture stationarily for 60 to 75 min so as to fractionate this blood sample into three layers, the upper, intermediate, and lower layers;
   (b) separating and collecting the upper layer from the other layers; and
   (c) treating the upper layer sample with hypotonic solution and then adding hypertonic solution into said upper layer sample.

9. The method of claim 8, including the step of providing a saponin solution as the hypotonic solution.

10. The method of claim 8, including the step of treating the upper layer with the hypotonic solution for substantially 30 seconds.

11. The method of claim 8, including the step of treating the upper layer with the hypotonic solution for a period sufficient to create an antibacterial sample.

12. The method of claim 11, including the step of treating the upper layer with the hypotonic solution for a period sufficient to preclude excessive hemolysis.

13. The method of claim 8, including the step of centrifuging the upper layer prior to treating the upper layer with the hypotonic solution.

14. The method of claim 13, including the steps of centrifuging the upper layer for a period sufficient to precipitate red blood cells and a clear layer, and discarding the clear layer.

15. Antibacterial material included in the solution produced by following steps;
   (a) mixing human blood sample with dextran aqueous solution and maintaining said mixture stationarily for 60 to 75 min so as to fractionate this blood sample into three layers, the upper, intermediate, and lower layers:
   (b) separating and collecting the upper layer from the other layers; and
   (c) treating the upper layer sample with hypotonic solution and then adding hypertonic solution into said upper layer sample.

16. The materials of claim 15, wherein the hyptonic solution is a saponin solution.

17. The material of claim 15, wherein the step of treating the upper layer with the hypotonic solution is for substantially 30 seconds.

18. The material of claim 17, wherein the step of treating the upper layer with the hypotonic solution is for a period sufficient to preclude excessive hemolysis.

19. The material of claim 15, wherein the step of treating the upper layer with the hypotonic solution is for a period sufficient to create an antibacterial sample.

20. The material of claim 15, wherein the upper layer is centrifuged prior to treating the upper layer with the hypotonic solution.

21. The material of claim 20, wherein the upper layer is centrifuged for a period sufficient to precipitate red blood cells and a clear layer, and discarding the clear layer.

* * * * *